US012102631B2

(12) United States Patent
Alcázar González et al.

(10) Patent No.: US 12,102,631 B2
(45) Date of Patent: Oct. 1, 2024

(54) QUINOLYLNITRONES FOR THE TREATMENT AND PREVENTION OF A CEREBRAL STROKE OR ISCHAEMIA

(71) Applicants: ISQUAEMIA BIOTECH, S.L., Madrid (ES); FUNDACIÓN PARA LA INVESTIGACIÓN BIOMÉDICA DEL HOSPITAL RAMÓN Y CAJAL (FIBIOHRC), Madrid (ES); CONSEJO SUPERIOR DE INVESTIGACIONES CIENTÍFICAS (CSIC), Madrid (ES)

(72) Inventors: Alberto Alcázar González, Madrid (ES); Emma Martínez Alonso, Madrid (ES); José Luis Marco Contelles, Madrid (ES); Mourad Chioua Asri, Madrid (ES); Juan José Montoya, Madrid (ES)

(73) Assignees: CONSEJO SUPERIOR DE INVESTIGACIONES CIENTÍFICAS (CSIC), Madrid (ES); FUNDACIÓN PARA LA INVESTIGACIÓN BIOMÉDICA DEL HOSPITAL RAMON Y CAJAL (FIBIOHRC), Madrid (ES); ISQUAEMIA BIOTECH, S.L., Madrid (ES)

( * ) Notice: Subject to any disclaimer, the term of this patent is extended or adjusted under 35 U.S.C. 154(b) by 583 days.

(21) Appl. No.: 17/284,181

(22) PCT Filed: Oct. 10, 2019

(86) PCT No.: PCT/EP2019/077525
§ 371 (c)(1),
(2) Date: Apr. 9, 2021

(87) PCT Pub. No.: WO2020/074666
PCT Pub. Date: Apr. 16, 2020

(65) Prior Publication Data
US 2021/0330662 A1    Oct. 28, 2021

(30) Foreign Application Priority Data
Oct. 10, 2018    (EP) ..................... 18382720

(51) Int. Cl.
*A61P 9/10* (2006.01)
*A61K 31/47* (2006.01)
*A61K 38/49* (2006.01)
*C07D 215/14* (2006.01)

(52) U.S. Cl.
CPC .............. *A61K 31/47* (2013.01); *A61K 38/49* (2013.01); *A61P 9/10* (2018.01); *C07D 215/14* (2013.01)

(58) Field of Classification Search
CPC ................................. C07D 215/14; A61P 9/10
See application file for complete search history.

(56) References Cited

FOREIGN PATENT DOCUMENTS

WO    WO 2013017715 A2    2/2013

OTHER PUBLICATIONS

Chemical Abstracts Registry No. 2281848-89-1, indexed in the Registry file on STN CAS Online on Mar. 8, 2019. (Year: 2019).*
Rowe, Raymond C, Paul J. Sheskey, and Marian E Quinn., Handbook of Pharmaceutical Excipients. London: Pharmaceutical Press , 6th Edition, 2009, pp. 766-770. (Year: 2009).*
Ayuso et al., "New Hierarchical Phosphorylation Pathway of the Translational Repressor eIF4E-binding Protein 1 (4E-BP1) in Ischemia-Reperfusion Stress," *Journal of Biological Chemistry* 285(45):34355-34363, Nov. 5, 2010. (9 pages).
Ayuso et al., "Quinolinyl Nitrone RP19 Induces Neuroprotection after Transient Brain Ischemia," *ACS Chem. Neurosci.* 8:2202-2213, Jul. 21, 2017. (12 pages).
Chioua et al., "α-Aryl-N-alkyl Nitrones, as Potential Agents for Stroke Treatment: Synthesis, Theoretical Calculations, Antioxidant, Anti-inflammatory, Neuroprotective, and Brain-Blood Barrier Permeability Properties," *J. Med. Chem.* 55:153-168, 2012. (16 pages).
García-Bonilla et al., "Regulatory proteins of eukaryotic initiation factor 2-alpha subunit (eIF2α) phosphatase, under ischemic reperfusion and tolerance," *Journal of Neurochemistry* 103:1368-1380, 2007. (13 pages).
Martín de la Vega et al., "Possible mechanisms involved in the down-regulation of translation during transient global ischaemia in the rat brain," *Biochem. J.* 357:819-826, 2001. (8 pages).
Quevedo et al., "Initiation Factor 2B Activity Is Regulated by Protein Phosphatase 1, Which Is Activated by the Mitogen-activated Protein Kinase-dependent Pathway in Insulin-like Growth Factor 1-stimulated Neuronal Cells," *Journal of Biological Chemistry* 278(19):16579-16586, 2003. (8 pages).

* cited by examiner

*Primary Examiner* — Laura L Stockton
(74) *Attorney, Agent, or Firm* — Seed IP Law Group LLP

(57) ABSTRACT

The invention relates to neuroprotective, antioxidant quinolylnitrones to which the blood-brain barrier is highly permeable, as potential drugs for the treatment of a cerebral stroke or ischaemia, Alzheimer's and Parkinson's disease and amyotrophic lateral sclerosis.

7 Claims, 9 Drawing Sheets

(A) Compounds from nitrones 3 and 4 by modification of the nitrone motif

6 (X= NOBn)
7 (X= NNH$_2$)
8 (X= NNHBn)
9 (X= NBn)
10 (X= N-*t*-Bu)

11

(B) Derivatives from nitrones 3 and 4 by modification of the substituent at C2

12 (X= H)
13 (X= OH)
14 (X= OMe)
15 (X= NHMe)
16 (X= NMe$_2$)

17

(C) Derivatives from nitrones 3 and 4 by modification of the substituents at ring A

18 (X= Cl)
19 (X= OH)

20 (X= Cl)
21 (X= OMe)

(C) Derivatives from nitrones 3 and 4 by modification of the substituents at ring A

22 (R= Me)
23 (R= t-Bu)
24 (R= Bn)

25 (X= OH)
26 (X= Cl)

27

28

(D) Miscellaneous compounds derived from nitrones 3 and 4

29 (R= Bn)
30 (R= t-Bu)

31

32

QUINOLYLNITRONES FOR THE TREATMENT AND PREVENTION OF A CEREBRAL STROKE OR ISCHAEMIA

TECHNICAL FIELD OF THE INVENTION

The present invention relates to the medical field, particularly to the use of quinolylnitrones for the treatment and prevention of a cerebral stroke or ischaemia.

BACKGROUND OF THE INVENTION

Oxidative stress is possibly one of the most important molecular events occurring during and after cerebral ischemic injury, and in particular their induction of damage to the membrane lipids. Current research efforts directed to find an efficient therapies for stroke, overcoming the limitations of the thrombolytic recombinant tissue plasminogen activator (rtPA) and thrombectomy-based therapeutic approaches, are mainly focused on the identification of new, more efficient neuroprotective agents able to block and scavenge reactive oxygenated species (ROS). This is due to the high susceptibility of neuronal membranes to be attacked by ROS through the allylic carbon of polyunsaturated fatty acids, main component of these brain structures. The resulting lipid hydroperoxide species are very unstable in vivo and, in the presence of bio-metals, such as iron salts, can be decomposed to new ROS, which will trigger further free radical cascade reactions. Potential consequences of membrane lipids damage include changes in fluidity, permeability, and orientation of proteins embedded in the bilayer of the plasma membrane, along with other cellular endo-membranes, leading finally to cell death in the brain tissue.

In this context, free radical scavengers, such as nitrones, have proved to be efficient neuroprotective agents in experimental ischemia studies. However, to date, no nitrone has been marketed for ischemic stroke treatment, due to failed clinical studies. This is the case of (Z)-α-phenyl-N-tert-butylnitrone (1, PBN) (FIG. 1), a simple but largely investigated nitrone that inhibits lipoprotein oxidation, reduces the oxidative damage to erythrocytes and the phenylhydrazine-induced peroxidation of lipids, and protects gerbils and mice from brain stroke and MPTP toxicity, respectively. In spite of this, nitrone 1 mechanism of action is still not clear. It does not seem due to its ability to act as a ROS trap, but to the suppression of inducible nitric oxide (NO) synthase expression, cytokine accumulation and apoptosis. On the other hand, the formation of NO from PBN spin adducts could also play a role in the observed effects in the central nervous system.

Another well-known nitrone is sodium (Z)-4-((tert-butyloxidoazanylidene)methyl)benzene-1,3-disulfonate (2, NXY-059) (FIG. 1), which based on its good neuroprotection in suitable animal models of transient and permanent focal ischemia, it was assayed in several clinical studies, unfortunately without success. In spite of these unfulfilled expectations, the current efforts devoted to discover new nitrones for the treatment of stroke show and proves that the antioxidant and neuroprotective strategy is still a choice for the development of new drugs for stroke.

In this context, the authors of the present invention have synthesized and biologically evaluated new nitrones as potential drugs for cerebral ischemia treatment. In one of these studies they identified quinolylnitrones (QNs) 3 and 4 (RP19) (FIG. 1) as potent antioxidant and neuroprotective agents. Remarkably, in the case of (Z)—N-benzyl-1-(2-chloro-6-methylquinolin-3-yl)methanimine oxide (4), the biological analysis showed that this nitrone induced long-term cell viability after 5 days of recovery after oxygen-glucose deprivation in primary neuronal cultures, and significantly reduced ROS and lipid peroxidation production. Furthermore, pharmacological treatment with nitrone 4 of reperfused animals after both global and focal ischemia, at the dose that was demonstrated to be neuroprotective in neuronal cultures, significantly decreased neuronal death and apoptosis induction, reduced the size of infarct, and improved the neurodeficit scores after 48 h or 5 days of reperfusion after ischemia.

With this background, and in order to improve the promising biological results gathered from nitrone 4, next we considered an in-depth exploration of the structure-activity relationship (SAR) on this QN, looking for new, more potent, efficient antioxidant and neuroprotective compounds for stroke.

Apoptosis was detected by the transferase mediated dUTP nick-end labeling (TUNEL) assay and visualized by fluorescence microscopy (in green). The images are representative results of the hippocampal CA1 (CA1) and cortical (C) regions from untreated and treated (23, 1.5 mg/kg) animals. TUNEL-positive cells were counted in CA1 and C fields as described in Methods (bar graph). Results represent the mean±SE of 6-12 individual animals. Error bars indicate SE (bar graph). **p<0.01, and *p<0.05, compared with their respective R5 d+vehicle by Dunnett's post test after ANOVA.

Figure 9:
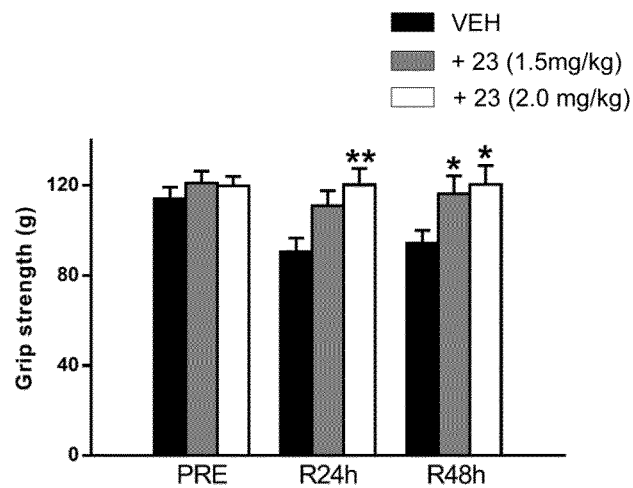

FIG. 9. Improvement of post-ischemic motor deficit after QN 23 treatment. QN 23 administered at the onset of the reperfusion after transient middle cerebral artery occlusion (tMCAO) improved grip strength values following 24 h and 48 h of reperfusion (R24 h and R48 h, respectively). Grip strength values corresponding to presurgery animals (PRE) are shown. Results represent the mean±SE of 8 individual animals. Error bars indicate SE (bar graph). *p<0.05, and **p<0.01, compared with vehicle treatment (VEH) by Bonferroni post test after two-way ANOVA.

Figure 10:
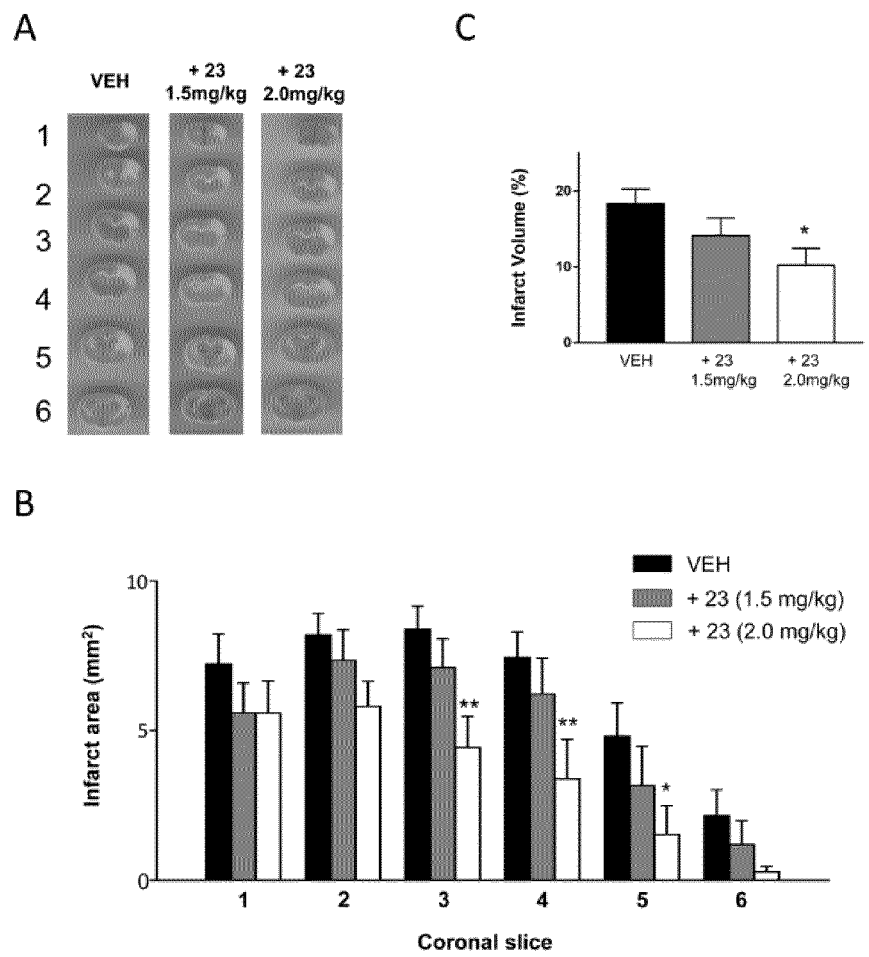

FIG. 10. QN 23 treatment reduces infarct size after transient middle cerebral artery occlusion (tMCAO). Representative images of TTC-stained brain sections of mice subjected to tMCAO are presented in (A). Six coronal sections (1 mm) of the rostro-caudal axis are shown. QN 23 administration decreased infarct area (B) and infarct volume (C) compared with vehicle treatment (VEH). Results represent the mean±SE of 8 individual animals. Error bars indicate SE (bar graph). *p≤0.05 compared with vehicle by Bonferroni post test after ANOVA.

Figure 11:
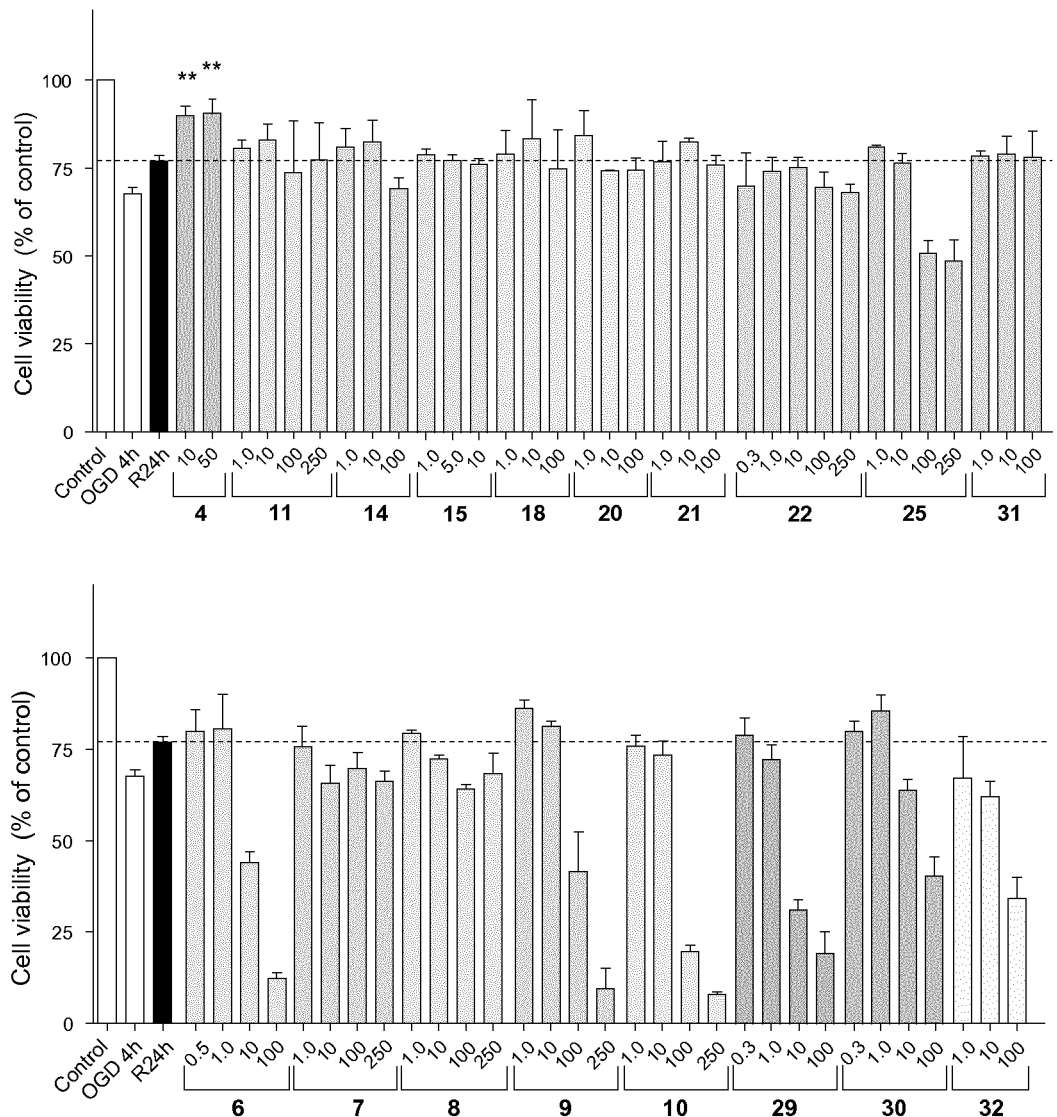

FIG. 11. Effect of QNs on primary neuronal cultures exposed to oxygen glucose deprivation (OGD). Bar chart showing the percentage of cell viability at 24 h of recovery after 4 h OGD, either untreated (R24 h) or treated with different concentrations (μM) of the QNs shown in the chart (see also Table 5).

SUMMARY OF THE INVENTION

Figure 1:
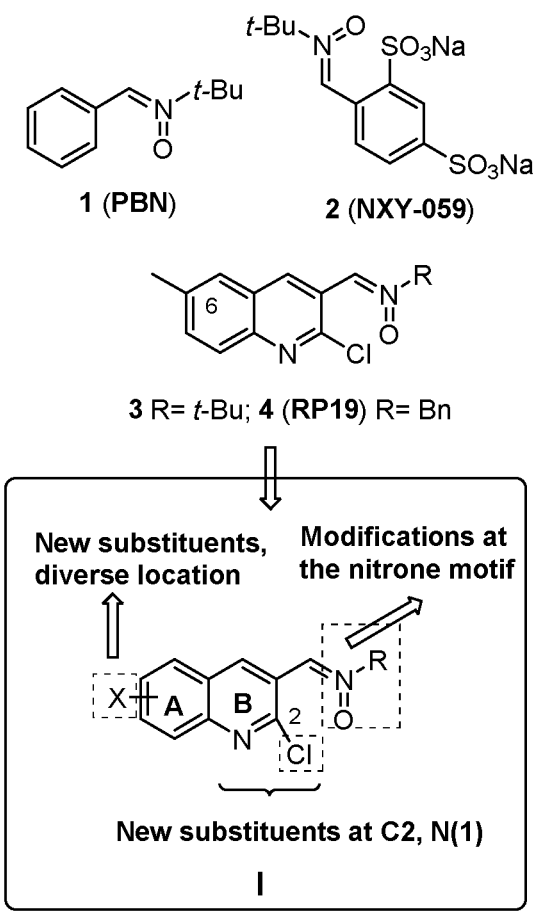
FIG. 1. Structure of nitrones 1-4, and the functional modifications incorporated leading to new quinolyl nitrones designed in this work (I).
Figure 2:
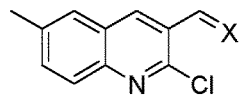
FIG. 2. Structures of the compounds investigated in the present invention.
Figure 2:
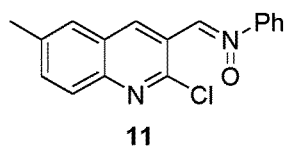
Figure 2:
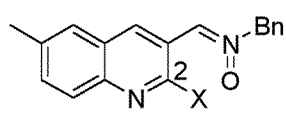
Figure 2:
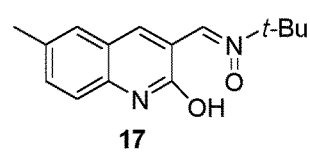
Figure 2:
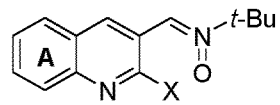
Figure 2:
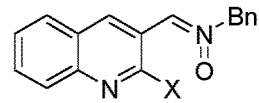
Figure 2:
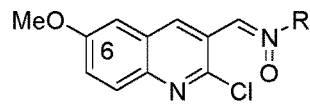
Figure 2:
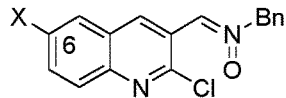
Figure 2:
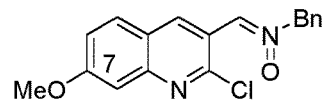
Figure 2:
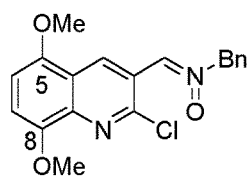
Figure 2:
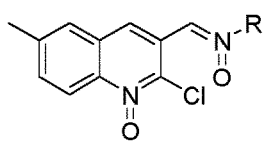
Figure 2:
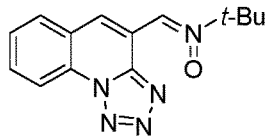
Figure 2:
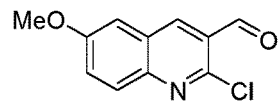

Nitrones 3 and 4 (FIG. 1) are simple, small molecules bearing a chloro and a methyl group at C2 and C6, and a N-butyl or N-benzylnitrone, respectively (FIG. 1). Starting from these two nitrones, as shown in FIG. 2, we have synthesized 31 new derivatives depicted in FIG. 2. They include 6 azo insaturated derivatives, (5-10, FIG. 2A), and 25 new nitrone-derived compounds (11-31, FIGS. 2A-D). These compounds have been obtained by means of four different modifications: (a) the nitrone group, including related unsaturated azo compounds such as oximes (5, 6), hydrazones (7, 8) or imines (9,10), the N-phenyl motif (11) (FIG. 2A); (b) the substituent at C2, by changing the chlorine for a hydrogen (12), hydroxyl (13,17), methoxy (14), N-methylamino (15) and N,N'-dimethylamino (16) groups (FIG. 2B); (c) the substituent at the aromatic ring A [H (18-21), C6-OMe (22-24), C6-OH (25), C6-Cl (26), C7-OMe (27), C5,C8-di-OMe (28)] (FIG. 2C); and (d) the addition of miscellaneous modifications such as N-oxide (29, 30), or a fused tetrazole ring (31). Finally, commercially available aldehyde 32 (FIG. 2D), was also included in the study for comparative purposes.

In the following sections we describe the identification of QN (Z)—N-t-butyl-1-(2-chloro-6-methoxyquinolin-3-yl) methanimine oxide (23) as a new and potent neuroprotective agent. As a new hit, nitrone 23 shows strong antioxidant capacity, and significantly increases neuronal viability in an in vitro model of ischemia. Also, it induces neuroprotection following in vivo ischemic reperfusion. Altogether, these capacities support it as a new potential drug for the treatment of stroke.

DESCRIPTION OF THE INVENTION

Abbreviations Used

AAPH, 2,2'-azobis(2-amidinopropane) dihydrochloride; ABTS, 2,2'-azino-bis(3-ethylbenzothiazoline-6-sulphonic acid; BBB, blood-brain barrier; CA, cornu ammonis; CNS, central nervous system; HAT, hydrogen atom transger; LDH, lactic acid dehydrogenase; LOX, lipoxygenase; LP, lipid peroxydation; MDA, malondialdehyde; MPTP, 1-methyl-4-phenyl-1,2,3,6-tetrahydropyridine; MTT, 3-(4, 5-dimethylthiazol-2-yl)-2,5-diphenyl tetrazolium bromide; NDGA, nordihydroguaiaretic acid; NDS, neurodeficit score; NO, nitric oxide; OGD, oxygen-glucose deprivation; ORTEP, oak ridge termal ellipsoid plot; PBN, phenyl-tert-butylnitrone; PBL, porcine brain lipid; QN, quinolyl nitrone; RA, reducing activity; ROS, reactive oxygen species; rtPA, recombinant tissue plasminogen activator; SAR, structure-activity relationship; SD, standard deviation; SNP, sodium nitroprusside; SET, single electron transfer; SNP, sodium nitroprusside; tMCAO, transiente middle cerebral artery occlusion; TTC, triphenyl tretrazolium chloride; TUNEL, terminal deoxynucleotidyl transferase-mediated dUTP nick-end labeling.

Description

We herein report the synthesis and neuroprotective capacity of a diverse array of 31 compounds (see FIG. 2) comprising quinolyloximes, quinolylhydrazones, quinolylimines, QNs, and related heterocyclic azolylnitrones.

We have observed that under OGD conditions, at the onset of recovery period after OGD, most of these QNs, but not the azo molecules, improved neuronal viability 24 h after recovery. Although no clear SAR could be proposed, we concluded that regarding the group attached to the nitrone moiety, the incorporation of a phenyl motif (compound 11, FIG. 2A), instead of a t-butyl (compound 3, FIG. 1) or a benzyl group (compound 4, FIG. 1) seems deleterious for the neuroprotective activity of the resulting QN. Similar observation can be made when a methyl group is the one implemented at the nitrone moiety (compare nitrone 22 with compounds 23 and 24, FIG. 2C).

For t-butyl nitrones 17-19, 23 and 31, the combination of functional groups MeO(C6)/Cl(C2) as shown in compound 23 gives better neuroprotection power than the no substitution at ring A/OH(C2) (compound 19) or the combination of functional groups Me(C6)/OH(C2) as shown in compound 17, and higher neuroprotection power than the no substitution at ring A/Cl(C2) (compound 18). The incorporation of a fused tetrazole ring onto the quinoline core, as in nitrone 31, gives no improvement for the neuroprotection compared with nitrones 18 or 19. Among the benzyl nitrones 12-16, 20, 21 and 24-28, the most potent, taking into account the mean values at the different dose concentrations, were compounds 12, 13, 16, 17, 19, 24 and 26-28 (FIG. 4), but none of them showed a clear better or higher neuroprotection than the others. This means that for benzyl nitrones, as shown before for t-butyl nitrones, no clear SAR can be defined, and a diverse array of functional group combination can afford good neuroprotection. Thus, regardless of the type, position or number of the groups in the ring A, and at C2, a quite similar neuroprotective effect was observed for QNs 24, 27 and 28. Surprisingly, Me(C6)nitrones 14 and 15, bearing a MeO and a NHMe at C2, respectively, were less potent than those bearing no substituent (12), OH (13) or NMe2 (16) at C2. Comparing Cl(C2) nitrones 25 and 26, the one bearing a Cl(C6) showed a better neuroprotective profile than the one bearing a OH(C6). Both no substituted nitrones at ring A, bearing a C1 atom (20) or a MeO (21) at C2, were poor neuroprotective compounds.

To sum up, we conclude that preferred functional groups leading to efficient neuroprotective activities are: (a) the nitrone group is effectively better than non-nitrone precursors or derivatives; (b) t-butyl or benzyl group at the nitrone moiety; (c) for t-butyl (or benzyl) nitrones, we have not found clear SAR, but a potent electron donor group at C6, such as the MeO with a Cl atom at C2 seems to afford the best neuroprotective effect.

Therefore, one aspect of the present invention refers to the antioxidant quinolylnitrones of formula I below as well as geometric isomers thereof. In addition, in a second aspect of the invention, it refers to the use of any of these neuroprotective compounds, to which the blood-brain barrier is highly permeable, as potential agents and drugs for the treatment of a cerebral stroke or ischaemia, Alzheimer's and Parkinson's disease and amyotrophic lateral sclerosis.

Compounds of formula I are described below,

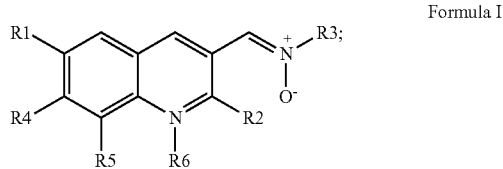

Formula I where, $R^1$ independently represents a hydrogen atom, a methyl ($CH_3$) group, a methoxy (MeO) group, or a hydroxyl group;

$R^2$ independently represents a hydrogen atom, hydroxyl, a chlorine, bromide or iodide atom, a methoxy group, and a —NH—$CH_3$, or —NH—$(CH_3)_2$ group; and $R^3$ independently represents a benzyl or tert-butyl moieties;

$R^4$ independently represents a hydrogen atom, a methyl ($CH_3$) group, a methoxy (MeO) group, or a hydroxyl group;

$R^5$ independently represents a hydrogen atom, a methyl ($CH_3$) group, a methoxy (MeO) group, or a hydroxyl group; and $R^6$ independently represents no atom, a hydrogen atom, or an Oxo group to form a second nitrone group.

Conventional though non-limiting examples of this family of compounds pertaining to formula I are:

Compounds of formula I, wherein $R^1$ is a methyl ($CH_3$) group, $R^3$ is a benzyl group, $R^4$ is a hydrogen atom, $R^5$ is a hydrogen atom, there is no radical in $R^6$, and $R^2$ represents a hydrogen atom, hydroxyl, a methoxy group, —NH—$CH_3$, or —NH—$(CH_3)_2$;

Compounds of formula I, wherein $R^1$ is a methyl ($CH_3$) group, $R^3$ is a tert-butyl group, and $R^2$ represents a hydroxy group;

Compounds of formula I, wherein $R^1$ is a hydrogen atom, $R^3$ is a tert-butyl moiety, $R^4$ is a hydrogen atom, $R^5$ is a hydrogen atom, there is no radical in $R^6$, and $R^2$ represents a chlorine atom, or a hydroxyl group;

Compounds of formula I, wherein $R^1$ is a hydrogen atom, $R^3$ is a benzyl moiety, $R^4$ is a hydrogen atom, $R^5$ is a hydrogen atom, there is no radical in $R^6$, and $R^2$ represents a chlorine atom, or a methoxy group;

Compounds of formula I, wherein $R^1$ is a methoxy group, $R^3$ is a methyl, benzyl or a tert-butyl moieties, $R^4$ is a hydrogen atom, $R^5$ is a hydrogen atom, there is no radical in $R^6$, and $R^2$ represents a chlorine atom; and Compounds of formula I, wherein $R^1$ is a hydroxyl group, $R^3$ is a benzyl group, R4 is a hydrogen atom, R5 is a hydrogen atom, there is no radical in R6, and $R^2$ represents a chlorine atom.

Further compounds not falling within formula I above such as compound 31 as identified in FIG. 2, are also part of the present invention, and in particular of the first aspect of the invention. Preferably these compounds are also used as potential agents and drugs for the treatment of a cerebral stroke or ischaemia, Alzheimer's and Parkinson's disease and amyotrophic lateral sclerosis, is also encompass herein.

From all the compounds tested, compound QN (Z)—N-t-butyl-1-(2-chloro-6-methoxyquinolin-3-yl)methanimine oxide (23), which structural formula (formula II) is described herein below:

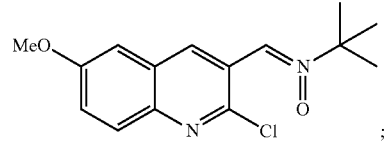

Formula II

Showed a striking antioxidant capacity against hydroxyl radicals and thus a remarkable activity for neuroprotection of primary cultured neurons after experimental ischemia. Certainly, the antioxidant analysis showed that QN 23 was able to trap the hydroxyl radical with a very strong and specific selectivity versus other ROS, supporting and confirming our target choice.

To explain these results, we have hypothesized that, as shown in Scheme 2, this is possibly due to the fact that the reaction of the toxic and highly reactive hydroxyl radical with QN 23 gives a new radical, extremely stable and non-toxic, due to its p-quinonoid mesomeric structure I (Scheme 2), where the presence of the electron-withdrawing chlorine atom affords additional stabilization degree.

Scheme 2. Reaction of hydroxyl radical with QN 23.

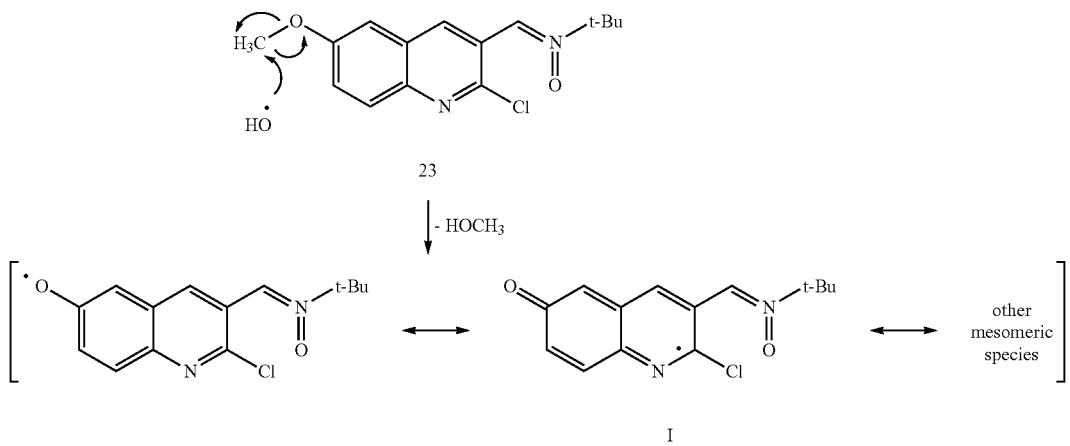

Finally, as QN 23 showed also neuroprotection induction in two in vivo models of global and focal cerebral ischemia, reducing significantly the neuronal death and infarct size after tMCAO, we conclude that QN 23 can be considered as a new extraordinary lead compound for ischemic stroke treatment. These invention demonstrate a success in finding potent neuroprotective agents supporting that the treatment of ischemic animals with novel nitrones improve their general neurological deficit score and reduces neuronal death in a much greater extent than nitrones 1 (PBN) or 2 (NXY-059), a fact that gives support and credit to the neuroprotection strategy to design new nitrones as small molecules for stroke therapy, compromised in the last decade by the failure of nitrone 2 in advanced clinical trials. A clinical failure explained, among other causes, by the poor BBB penetration of nitrone 2, with a log BB value of −1.9, which compares very unfavorably with the calculated value for QN 23 (log BB, 0.47).

Thus, in preferred embodiment of the first or second aspect of the invention, the compound of formula I is compound QN 23.

In a further preferred embodiment of the first or second aspect of the invention or of any of its preferred embodiments, pharmaceutically acceptable pro-drugs, polymorphs, salts and hydrates of any of the above compounds of formula I are included within the present invention.

On the other hand, it is noted that any of the compounds mentioned as examples throughout the present invention can be used separately or in combination, particularly as adjuvant therapy administered simultaneously, alternatively or successively with respect to a first-line therapy suitable for the treatment of a neurological disease, such as cerebral ischaemia, Alzheimer's disease, Parkinson's disease and amyotrophic lateral sclerosis. In this sense, the quinolylnitrones of formula I administered simultaneously, alternatively or successively with respect to a thrombolytic agent/s and/or thrombectomy procedures, result in particularly suitable therapy for the treatment of cerebral ischaemia, particularly acute cerebral ischaemia.

Therefore, a third aspect of the present invention relates to a composition comprising any quinolylnitrone derivative of formula I, and geometric isomers thereof, as defined in the first aspect of the invention, for use as adjuvant therapy administered simultaneously, alternatively or successively with respect to a first-line therapy suitable for the treatment of a neurological disease, such as cerebral ischaemia, Alzheimer's disease, Parkinson's disease and amyotrophic lateral sclerosis. The quinolylnitrone derivative is preferably QN 23.

Another aspect of the present invention relates to a pharmaceutical composition comprising the compound of formula I, pharmaceutically suitable excipients, and optionally a thrombolytic agent.

Another aspect of the present invention relates to a composition comprising the quinolylnitrone derivative defined above, preferably the quinolylnitrone derivative QN 23, for the preparation of a medicament for use as adjuvant therapy administered simultaneously, alternatively or successively with respect to a first-line therapy suitable for the treatment of the cerebral ischaemia, where said primary or first-line treatment comprises the use of a thrombolytic agent, preferably the use of tissue plasminogen activator (rt-PA), and/or thrombectomy procedures.

Additionally, the present invention relates to a method for identifying and evaluating, in a rapid and optionally robotic manner, compounds having high neuroprotective power and involving a possible effective treatment for neurological diseases, such as cerebral ischaemia, Alzheimer's disease, Parkinson's disease and amyotrophic lateral sclerosis.

Quinolylnitrone derivatives of formula I and geometric isomers thereof are used to carry out said drug screening. To verify the neuroprotective activity of said quinolylnitrones of formula I and to enable selecting those compounds with the highest activity, their neuroprotective power is determined using any in vitro or in vivo model or assay suited to that end. Said models or assays are known for the person skilled in the art; nevertheless, and merely by way of example, a possible assay for determining the neuroprotective activity of quinolylnitrones of formula I and their possible usefulness in the treatment of neurological diseases, would be in primary neuronal cultures, cultured from 6 to 8 days, taken from the cerebral cortex of rats, where cell viability is determined (Quevedo, C, Salinas, M, Alcázar, A. Initiation factor 2B activity is regulated by protein phosphatase 1, which is activated by the mitogen-activated protein kinase-dependent pathway in insulin-like growth factor 1-stimulated neuronal cells. J. Biol. Chem. 2003, 278, 16579-16586), and subjected to oxygen-glucose deprivation (OGD) (Chioua M, Sucunza D, Soriano E, Hadjipavlou-Litina D, Alcázar A, Ayuso I, Oset-Gasque M J, González M P, Monjas L, Rodríguez-Franco M I, Marco-Contelles J, Samadi A. α-aryl-N-alkyl nitrones, as potential agents for stroke treatment: synthesis, theoretical calculations, antioxidant, anti-inflammatory, neuroprotective, and brain-blood barrier permeability properties. J Med Chem. 2012, 55, 153-168), according to the following protocol:

Cell viability is measured using 3-(4,5-dimethylthiazol-2-yl)-2,5-diphenyl tetrazolium bromide (MTT). Therefore, exposure of the neuronal cultures to OGD for 4 h (OGD 4 h) induces a significant decrease in cell viability of 67.3% ($p<0.0001$ versus 100% control, one-sample test), which is partially reverted 24 hours after reperfusion (R24 h, 76.1%; $p<0.0022$ versus OGD 4 h, Student's t-test), but it does not reach the control value at 24 h ($p<0.0001$ versus 100% control, one-sample t-test). In this sense, to evaluate the neuroprotective power of the quinolylnitrones of formula I, they are added to the primary culture at the beginning of the reperfusion period, using compound 2 (NXY-059) as reference. Those quinolylnitrones of formula I having higher neuroprotective power with respect to compound 2 are selected.

Additionally and also by way of example, a second model which allows selecting those quinolylnitrones of formula Ia-c having higher neuroprotective power would be by inducing global ischaemia in adult rats according to the conventional four-vessel occlusion method [(a) Martín de la Vega C, Burda J, Nemethova M, Quevedo C, Alcázar A, Martin M E, Salinas M. Possible mechanisms involved in the down-regulation of translation during transient global ischaemia in the rat brain. Biochem J 2001, 357, 819-826; (b) García-Bonilla L, Cid C, Alcázar A, Burda J, Ayuso I, Salinas M. Regulation proteins of eukaryotic initiation factor 2-alpha subunit (eIF2a) phosphatase, under ischemic reperfusion and tolerance. J Neurochem 2007, 103, 1368-1380; (c) Ayuso M I, Hernández-Jiménez M, Martin M E, Salinas M, Alcázar A. New hierarchical phosphorylation pathway of the translational repressor eIF4E-binding protein 1 (4E-BP1) in ischaemia-reperfusion stress. J Biol Chem 2010, 285, 34355-34363].

The following examples serve to illustrate the present invention but in no case are limiting thereof.

EXAMPLES

Materials and Methods

General Methods. Reactions were monitored by TLC using precoated silica gel aluminium plates containing a fluorescent indicator (Merck, 5539). Detection was done by UV (254 nm) followed by charring with sulfuric-acetic acid spray, 1% aqueous potassium permanganate solution or 0.5% phosphomolybdic acid in 95% EtOH. Anhydrous $Na_2SO_4$ was used to dry organic solutions during work-ups and the removal of solvents was carried out under vacuum with a rotary evaporator. Flash column chromatography was performed using silica gel 60 (230-400 mesh, Merck). Melting points were determined on a Kofler block and are uncorrected. IR spectra were obtained on a Perkin-Elmer Spectrum One spectrophotometer. $^1H$ NMR spectra were recorded with a Varian VXR-200S spectrometer, using tetramethylsilane as internal standard and $^{13}C$ NMR spectra were recorded with a Bruker WP-200-SY. All the assignments for protons and carbons were in agreement with 2D COSY, HSQC, HMBC, and 1D NOESY spectra. Values with (*) can be interchanged. The purity of compounds was checked by elemental analyses, conducted on a Carlo Erba EA 1108 apparatus, and confirmed to be >95%. 1,1-Diphenyl-2-picrylhyrazyl (DPPH) radical, Nordihydroguaiaretic acid (NDGA), trolox, 2,2'-azobis(2-amidinopropane) dihydrochloride (AAPH), Soybean LOX linoleic acid sodium salt were purchased from the Aldrich Chemical Co. Milwaukee, WI, (USA). Phosphate buffer (0.1 M and pH 7.4) was prepared mixing an aqueous $KH_2PO_4$ solution (50 mL, 0.2 M), and an aqueous of NaOH solution (78 mL, 0.1 M); the pH (7.4) was adjusted by adding a solution of $KH_2PO_4$ or NaOH. For the in vitro tests a Lambda 20 (Perkin-Elmer-PharmaSpec 1700) UV-Vis double beam spectrophotometer was used.

General Procedure for nitrones synthesis. In a 20 mL glass tube equipped with septa, the aldehyde, dry $Na_2SO_4$ (3 equiv), and triethylamine (2 equiv) were suspended in dry THF or EtOH. Then, hydroxylamine hydrochloride (1.5 equiv) was added. The mixture was stirred for 30 s and then exposed to MWI (250 W) at 90° C. during the time indicated for each compound. When the reaction was complete (tlc analysis), the reaction mixture was diluted with water, extracted with AcOEt, dried over anhydrous sodium sulfate, filtered, and the solvent evaporated. The resultant crude mixture was purified by column chromatography.

(Z)-1-(2-Chloro-6-methylquinolin-3-yl)-N-phenylmethanimine oxide (11). To a solution of 2-chloro-6-methylquinoline-3-carbaldehyde (154 mg, 0.75 mmol) and $MgSO_4$ (181 mg, 1.5 mmol) in EtOH (10 mL), N-phenylamine was added (100 mg, 0.9 mmol) followed by $Et_3N$ (0.14 mL, 1 mmol). After 3 h of reaction and column cromatography (hexane/EtOAc, 85:15, v/v), the nitrone 11 (133 mg, 60%) was obtained as a palid yellow solid: mp 134-6° C.; IR (KBr) vmax 3401, 3059, 2920, 1572, 1486, 1461, 1139, 1184, 1048 $cm^{-1}$; $^1H$ NMR (400 MHz, DMSO-$d_6$) δ 10.30 (d, J=0.9 Hz, 1H, H-4'), 8.57 (d, J=0.6 Hz, 1H, HC=N), 7.94-7.88 (m, 3H, Ar), 7.85 (d, J=8.6 Hz, 1H, Ph), 7.70 (dd, J=8.6, 1.9 Hz, 1H, Ph), 7.61-7.54 (m, 1H, Ph), 2.49 (s, 1H, $CH_3$); $^{13}C$ NMR (101 MHz, DMSO-$d_6$) δ 149.4 (Ph), 147.9, 145.6, 138.6 (3Ar), 136.4 (C-4') 134.9, 131.2, 130.1 (4Ph), 129.3 (C=N), 128.6 (C-5', Ar), 128.1 (Ph), 127.1, 123.3 (2Ar), 122.3 (2Ar), 21.8 ($CH_3$); MS (ESI) m/z: 297.0 $(M+H)^+$. Anal. Calcd for $C_{17}H_{13}ClN_2O+⅙H_2O$: C, 68.12; H, 4.48; N, 9.35. Found: C, 68.07; H, 4.48; N, 9.73.

6-Methylquinoline-3-carbaldehyde. To a solution of 2-chloro-6-methylquinoline-3-carbaldehyde (205 mg, 1 mmol, 1 equiv) and $Pd(PPh_3)_4$ (115 mg, 0.1 mmol, 0.1 eq), $Et_3N$ (0.8 mL, 6 mmol, 6 equiv) in DMF (10 mL) was added formic acid (276 mg, 5.4 mmol, 5.4 equiv) dropwise over 2 min. The reaction mixture was warmed to 110° C. over 1.5 h. Then, the reaction was diluted (water), extracted with ethyl acetate, washed with brine, dried over $Na_2SO_4$, filtered and evaporated to dryness to give the crude product, which was purified by column chromatography (hexane/ethyl acetate 8/2) to give 6-methylquinoline-3-carbaldehyde, yield as white solid (134 mg, 78%): $^1H$ NMR (300 MHz, $CDCl_3$) δ 10.24 (s, 1H, CHO), 9.30 (s, 1H, H-2), 8.54 (d, J=2.2 Hz, 1H, H-4), 8.08 (d, J=8.5 Hz, 1H, H-5), 7.72 (dd, J=8.5, 2.2 Hz, 2H, H-7, H-8), 2.59 (s, 3H, $CH_3$); MS (ESI) m/z: 277 $(M+H)^+$.

(Z)—N-Benzyl-1-(6-methylquinolin-3-yl)methanimine oxide (12). Following the general procedure, reaction of 6-methylquinoline-3-carbaldehyde (171 mg, 1 mmol), $Na_2SO_4$ (410 mg, 3 mmol), $Et_3N$ (0.30 mL, 2 mmol), and N-benzylhydroxylamine hydrochloride (239 mg, 1.5 mmol) in THF (15 mL), after 5 h, and column chromatography (hexane/EtOAc, 1:1, v/v), gave nitrone 12 (265 mg, 96%) as a yellow liquid: IR (KBr) $v_{max}$ 3037, 1563, 1498, 1460, 1143 $cm^{-1}$; $^1H$ NMR (300 MHz, $CDCl_3$) δ 9.78 (s, 1H, H-2), 8.83 (s, 1H, H-4), 7.95 (d, J=8.6 Hz, 1H, H-7), 7.61 (m, 2H, N=CH, H-5), 7.47 (m, 5H, Ph), 5.15 (s, 2H, $CH_2Ph$), 2.53

(s, 3H, CH$_3$); $^{13}$C NMR (101 MHz, CDCl$_3$) δ 149.9 (CH, C-2), 147.2 (C, C-8a), 137.6 (C, C-6), 134.5 (CH, C-4), 133.5 (CH, C-7), 133.3 (C, C-1'), 132.1 (CH, N=CH), 129.7 (2CH, Ph), 129.6 (CH, Ph), 129.5 (2CH, Ph), 129.1 (CH, C-5), 128.3 (CH, C-8), 128.0 (C, C-4a), 124.1 (C, C-3), 71.9 (CH$_2$), 22.0 (CH$_3$); MS (ESI) m/z: 277 [M+1]$^+$, 299 [M+Na]$^+$, 553 [2M+1]$^+$, 575 [2M+Na]$^+$; Anal. Calcd. for C$_{18}$H$_{16}$N$_2$O: C, 78.24; H, 5.84; N, 10.14; Found: C, 78.12; H, 6.01; N, 10.22.

(Z)—N-Benzyl-1-(6-methyl-2-oxo-1,2-dihydroquinolin-3-yl)methanimine oxide (13). Following the general procedure, reaction of 6-methyl-2-oxo-1,2-dihydroquinoline-3-carbaldehyde[47] (187 mg, 1 mmol), Na$_2$SO$_4$ (410 mg, 3 mmol), Et$_3$N (0.3 mL, 2 mmol), and N-benzylhydroxylamine hydrochloride (239 mg, 1.5 mmol) in THF (15 mL), after 1.5 h, and column chromatography (hexane/EtOAc, 7:3, v/v), gave nitrone 13 (184 mg, 63%) as a solid: mp 274-5° C.; IR (KBr) ν$_{max}$ 3029, 2919, 1673, 1498, 1409, 1224, 1135 cm$^{-1}$; $^1$H NMR (500 MHz, DMSO-d$_6$) δ 11.94 (s, 1H, NH), 9.74 (s, 1H, H-4), 8.21 (d, J=0.6 Hz, 1H, N=CH), 7.49 (m, 2H, Ph), 7.44 (m, 1H, H-5), 7.37 (m, 3H, Ph), 7.33 (ddd, J=8.3, 1.9, 0.6 Hz, 1H, H-7), 7.17 (d, J=8.3 Hz, 1H, H-8), 5.16 (s, 2H, CH$_2$Ph), 2.31 (d, J=0.7 Hz, 3H, CH$_3$); $^{13}$C NMR (126 MHz, DMSO-d6) δ 160.6 (C=O), 136.9 (C, C-8a), 135.9 (CH, C-4), 135.1 (C, C-1'), 133.0 (CH, C-7), 131.9 (C, C-6), 129.6 (2CH-arom), 128.9 (2CH-arom), 128.8 (CH, C-5), 128.5 (CH, N=CH), 122.6 (C, C-3), 119.5 (C, C-4a), 115.4 (CH, C-8), 70.7 (CH$_2$), 20.8 (CH$_3$); MS (ESI) m/z: 293 [M+1]$^+$, 315 [M+Na]$^+$. Anal. Calcd. for C$_{18}$H$_{16}$N$_2$O$_2$: C, 73.95; H, 5.52; N, 9.58; Found: C, 74.02; H, 5.42; N, 9.31

(Z)—N-Benzyl-1-(2-methoxy-6-methylquinolin-3-yl)methanimine oxide (14). Following the general procedure, reaction of 2-methoxy-6-methylquinoline-3-carbaldehyde[48] (201 mg, 1 mmol), Na$_2$SO$_4$ (410 mg, 3 mmol), Et$_3$N (0.30 mL, 2 mmol), and N-benzylhydroxylamine hydrochloride (239 mg, 1.5 mmol) in EtOH (15 mL), after 3 h, and column chromatography (hexane/EtOAc, 9:1, v/v), gave nitrone 14 (92 mg, 30%) as a pale yellow solid: mp 142-4° C.; IR (KBr) ν$_{max}$ 2943, 1595, 1447, 1344, 1257 cm$^{-1}$; $^1$H NMR (400 MHz, CDCl$_3$) δ 10.02 (s, 1H, H-4), 8.03 (s, 1H, N=CH), 7.67 (d, J=8.5 Hz, 1H), 7.52-7.50 (m, 3H, 2H-Ph+H-5), 7.42 (m, 4H, 3H-Ph+H-7), 5.10 (s, 2H, CH$_2$), 4.07 (s, 3H, OCH$_3$), 2.45 (s, 3H, CH$_3$); $^{13}$C NMR (101 MHz, cdcl$_3$) δ 158.3 (CH, C-2), 144.9 (C, C-8a), 137.0 (CH, C-4), 134.4 (C, C-6), 133.6 (C, C-1'), 133.0 (CH, C-4'), 129.3 (2CH-Ph), 129.2 (CH, C-7), 129.1 (2CH-Ph), 128.7 (CH, N=CH), 128.3 (CH, C-5), 126.7 (CH, C-8), 125.2 (C, C-4a), 115.2 (C, C-3), 71.9 (CH$_2$), 53.9 (OCH$_3$), 21.5 (CH$_3$); MS (ESI) m/z: 307 [M+1]$^+$, 329 [M+Na]$^+$. Anal. Calcd. for C$_{19}$H$_{18}$N$_3$O$_2$: C, 74.49; H, 5.92; N, 9.14. Found: C, 74.28; H, 6.04; N, 9.02.

(Z)—N-Benzyl-1-(6-methyl-2-(methylamino)quinolin-3-yl)methanimine oxide (15). Following the general procedure, reaction of 6-methyl-2-(methylamino)quinoline-3-carbaldehyde[49] (205 mg, 1 mmol), Na$_2$SO$_4$ (410 mg, 3 mmol), Et$_3$N (0.30 mL, 2 mmol), and N-benzylhydroxylamine hydrochloride (239 mg, 1.5 mmol) in EtOH (15 mL), after 1 h, and column chromatography (hexane/EtOAc, 7:3, v/v), gave nitrone 15 (205 mg, 67%) as a white solid: mp 195-7° C.; IR (KBr) ν$_{max}$ 3337, 1596, 1533, 1395, 1143 cm$^{-1}$; $^1$H NMR (400 MHz, CDCl$_3$) δ 8.18 (s, 1H, H-4), 7.61 (d, J=8.5 Hz, 1H, H-7), 7.53 (d, J=0.7 Hz, 1H, N=CH), 7.46 (m, 5H, Ph), 7.39 (d, J=8.5 Hz, 1H, H-8), 7.31 (dd, J=2.1, 1.1 Hz, 1H, H-5), 6.86 (d, J=5.2 Hz, 1H, NH), 5.11 (s, 2H, CH$_2$), 3.09 (d, J=4.7 Hz, 3H, NHCH$_3$), 2.41 (d, J=0.9 Hz, 3H, CH3); $^{13}$C NMR (101 MHz, CDCl$_3$) δ 154.9 (C, C-2), 147.6 (C, C-8a), 139.6 (CH, C-4), 134.6 (C, C-6), 133.4 (CH, C-7), 133.0 (C, C1'), 132.0 (CH, N=CH), 129.5 (CH, H-4'), 129.4 (2CH-Ph), 129.4 (2CH-Ph), 127.3, 126.3, 122.3, 114.4, 71.1, 28.9, 21.3; MS (ESI) m/z: 306 [M+1]$^+$, 328 [M+Na]$^+$. Anal. Calcd. for C$_{19}$H$_{19}$N$_3$O: C, 74.73; H, 6.27; N, 13.76. Found: C, 74.42; H, 6.09; N, 13.93.

(Z)—N-Benzyl-1-(2-(dimethylamino)-6-methylquinolin-3-yl)methanimine oxide (16). Following the general procedure, reaction of 2-(dimethylamino)-6-methylquinoline-3-carbaldehyde[49] (214 mg, 1 mmol), Na$_2$SO$_4$ (410 mg, 3 mmol), Et$_3$N (0.30 mL, 2 mmol), and N-benzylhydroxylamine hydrochloride (239 mg, 1.5 mmol) in THF (15 mL), after 2.5 h, and column chromatography (hexane/EtOAc, 3:2, v/v), gave nitrone 16 (309 mg, 97%) as a pale yellow solid: mp 189-191° C.; IR (KBr) ν$_{max}$ 2919, 1688, 1628, 1591, 1394 cm$^{-1}$; $^1$H NMR (400 MHz, CDCl$_3$) δ 9.93 (s, 1H, H-4), 7.68 (d, J=8.6 Hz, 1H, H-7), 7.66 (s, 1H, N=CH), 7.53 (d, J=8.6 Hz, 1H, H-8), 7.51 (m, 2H, H-5, H-4' Ph), 7.44 (m, 4H, Ph), 5.13 (s, 2H, CH$_2$Ph), 2.86 [s, 6H, N(CH$_3$)$_2$], 2.46 (s, 3H, CH$_3$); $^{13}$C NMR (101 MHz, DMSO-d$_6$) δ 159.9 (C, C-2), 145.9 (C, C-8a), 136.9 (CH, C-4), 134.5 (C, C-6), 133.7 (C, C1'), 133.2 (CH, C-7), 131.7 (CH, N=CH), 129.8, 129.5, 128.2 (5CH, Ph), 127.4 (CH, C-5), 125.2 (CH, C-8), 117.4 (C, C-4a), 117.4 (C, C-3), 72.1 (PhCH$_2$), 43.4 (2CH$_3$), 21.7 (CH$_3$); MS (ESI) m/z: 320 [M+1]$^+$, 342 [M+Na]$^+$. Anal. Calcd. for C$_{20}$H$_{21}$N$_3$O: C, 75.21; H, 6.63; N, 13.16. Found: C, 74.98; H, 6.92; N, 12.97.

(Z)—N-tert-Butyl-1-(6-methyl-2-oxo-1,2-dihydroquinolin-3-yl)methanimine oxide (17). Following the general procedure, reaction of 6-methyl-2-oxo-1,2-dihydroquinoline-3-carbaldehyde[50] (187 mg, 1 mmol), Na$_2$SO$_4$ (410 mg, 3 mmol), Et$_3$N (0.30 mL, 2 mmol), and N-(tert-butyl)hydroxylamine hydrochloride (188 mg, 1.5 mmol) in THF (15 mL), after 1.5 h, and column chromatography (hexane/EtOAc, 7:3, v/v), gave nitrone 17 (187 mg, 73%) as a solid: mp 231-3° C.; IR (KBr) ν$_{max}$ 2978, 2917, 1650, 1557, 1403, 1222, 1145 cm$^{-1}$; $^1$H NMR (500 MHz, CDCl$_3$) δ 11.26 (s, 1H, NH), 10.09 (m, 1H, H-4), 8.31 (d, J=0.6 Hz, 1H, N=CH), 7.41 (m, 1H, H-5), 7.34 (m, 1H, H-7), 7.20 (d, J=8.3 Hz, 1H, H-8), 2.40 (t, J=0.7 Hz, 3H, CH$_3$), 1.66 (s, 9H, 3CH$_3$); $^{13}$C NMR (126 MHz, CDCl$_3$) δ 162.4 (C=O), 137.8 (CH, C-4), 135.9 (C, C-3), 132.8 (CH, C-7), 132.7 (C—C-6), 129.0 (CH, C-5), 124.9 (CH, N=CH), 122.0 (C, C-4a), 120.4 (C, C-8a), 115.2 (CH, C-8), 71.6 (C, C(CH$_3$)$_3$), 28.3 (3CH$_3$), 20.9 (CH$_3$); MS (ESI) m/z: 259 [M+1]$^+$, 281 [M+Na]$^+$, 539 [2M+Na]$^+$. Anal. Calcd. for C$_{15}$H$_{18}$N$_2$O$_2$: C, 69.74; H, 7.02; N, 10.84. Found: C, 69.91; H, 7.00; N, 10.64.

(Z)—N-t-Butyl-1-(2-chloroquinolin-3-yl)methanimine oxide (18). Following the general procedure, reaction of commercial 2-chloroquinoline-3-carbaldehyde (191 mg, 1 mmol), Na$_2$SO$_4$ (410 mg, 3 mmol), Et$_3$N (0.30 mL, 2 mmol), and N-(tert-butyl)hydroxylamine hydrochloride (188 mg, 1.5 mmol) in EtOH (10 mL), after 3.5 h, and column chromatography (hexane/EtOAc, 8:2, v/v), gave nitrone 18 (215 mg, 82%) as a white solid: mp desc. ° C.; IR (KBr) ν$_{max}$ 2977, 1551, 1365, 1184, 1047 cm$^{-1}$; $^1$H NMR (400 MHz, CDCl$_3$) δ 10.38 (s, 1H, H-4), 8.28 (s, 1H, N=CH), 7.94 (d, J=8.5 Hz, 1H, H-5), 7.87 (d, J=8.1 Hz, 1H, H-8), 7.72 (ddd, J=8.4, 7.0, 1.4 Hz, 1H, H-7), 7.54 (ddd, J=8.1, 7.1, 1.1 Hz, 1H, H-6), 1.66 (s, 9H, 3CH$_3$); $^{13}$C NMR (101 MHz, CDCl$_3$) δ 149.0 (C, C-2), 147.1 (C, C8a), 137.2 (CH, C-4), 131.6 (CH, C-8), 129.2 (CH, C-7), 128.3 (CH, C-5), 127.8 (CH, C-6), 127.4 (C, C-4a), 125.4 (CH, N=CH), 123.0 (C, C-3), 72.7 (C, C(CH$_3$)$_3$), 28.5 (3CH$_3$); MS (ESI) m/z: 263 [M+1]$^+$, 285 [M+Na]$^+$. Anal. Calcd. for C$_{14}$H$_{15}$ClN$_2$O: C, 64.00; H, 5.75; N, 10.66. Found: C, 63.89; H, 5.94; N, 10.62.

(Z)—N-tert-Butyl-1-(2-oxo-1,2-dihydroquinolin-3-yl)methanimine oxide (19). Following the general procedure, reaction of commercial 2-oxo-1,2-dihydroquinoline-3-carbaldehyde (173 mg, 1 mmol), Na$_2$SO$_4$ (410 mg, 3 mmol), Et$_3$N (0.30 mL, 2 mmol), and N-(tert-butyl)hydroxylamine hydrochloride (188 mg, 1.5 mmol) in EtOH (10 mL), after 3 h, and column chromatography (hexane/EtOAc, 2:3, v/v), gave nitrone 19 (227 mg, 93%) as a white solid: mp 206-9° C.; IR (KBr) $v_{max}$ 2940, 2885, 2850, 1660, 1549, 1153 cm$^{-1}$; $^1$H NMR (400 MHz, CDCl$_3$) δ 11.72 (s, 1H, NH), 10.17 (s, 1H, H-4), 8.33 (s, 1H, N=CH), 7.64 (dd, J=7.9, 1.3 Hz, 1H, H-5), 7.52 (ddd, J=8.5, 7.2, 1.4 Hz, 1H, H-6), 7.34 (d, J=8.3 Hz, 1H, H-8), 7.23 (ddd, J=8.2, 7.3, 1.1 Hz, 1H, H-7), 1.67 (s, 9H, 3CH$_3$); $^{13}$C NMR (101 MHz, CDCl$_3$) δ 163.0 (C=O), 138.2 (CH, C-4), 138.1 (C, C-3), 131.5 (CH, C-6), 129.7 (CH, C-5), 125.0 (CH, N=CH), 123.4 (CH, C-7), 122.3 (C, C-4a), 120.6 (C, C-8a), 115.7 (CH, C-8), 71.9 (C, C(CH$_3$)$_3$), 28.5 (3CH$_3$); MS (ESI) m/z: 245 [M+1]$^+$, 267 [M+Na]$^+$, 511 [2M+Na]$^+$. Anal. Calcd. for C$_{14}$H$_{16}$N$_2$O$_2$: 68.83; H, 6.60; N, 11.47. Found: C, 68.23; H, 6.92; N, 12.07.

(Z)—N-Benzyl-1-(2-chloroquinolin-3-yl)methanimine oxide (20). Following the general procedure, reaction of commercial 2-chloroquinoline-3-carbaldehyde (191 mg, 1 mmol), Na$_2$SO$_4$ (410 mg, 3 mmol), Et$_3$N (0.30 mL, 2 mmol), and N-benzylhydroxylamine hydrochloride (239 mg, 1.5 mmol) in EtOH (10 mL), after 3 h, and column chromatography (hexane/EtOAc, 3:2, v/v), gave nitrone 20 (220 mg, 74%) as a white solid: mp 144-6° C.; IR (KBr) $v_{max}$ 3070, 1555, 1484, 1332, 1187 cm$^{-1}$; $^1$H NMR (400 MHz, CDCl$_3$) δ 10.28 (s, 1H, H-4), 8.11 (s, 1H, N=CH), 7.93 (d, J=8.4 Hz, 1H, H-5), 7.85 (d, J=8.2 Hz, 1H, H-8), 7.72 (ddd, J=8.4, 7.0, 1.4 Hz, 1H, H-6), 7.55 (m, 1H, H-7), 7.52 (m, 2H, Ph), 7.43 (m, 3H, Ph), 5.15 (s, 2H, CH$_2$); $^{13}$C NMR (101 MHz, CDCl$_3$) δ 148.4 (C, C-2), 147.2 (C, C-8a), 137.6 (CH, C-4), 132.9 (C, C-1'), 131.9 (CH, C-7), 129.6 (2CH-Ph), 129.6 (CH, C-4'), 129.3 (2CH-Ph), 129.2 (CH, N=CH), 128.3 (CH, C-5), 127.9 (CH, C-8), 127.2 (C, C-4a), 122.5 (C—C-3), 72.5 (CH2); MS (ESI) m/z: 297 [M+1]$^+$, 319 [M+Na]$^+$, 615 [2M+Na]$^+$. Anal. Calcd. for C$_{17}$H$_{13}$ClN$_2$O: C, 68.81; H, 4.42; N, 9.44. Found: C, 68.52; H, 4.04; N, 9.50.

(Z)—N-Benzyl-1-(2-methoxyquinolin-3-yl)methanimine oxide (21). Following the general procedure, reaction of commercial 2-methoxyquinoline-3-carbaldehyde (187 mg, 1 mmol), Na$_2$SO$_4$ (410 mg, 3 mmol), Et$_3$N (0.30 mL, 2 mmol), and N-benzylhydroxylamine hydrochloride (239 mg, 1.5 mmol) in EtOH (15 mL), after 3.5 h, and column chromatography (hexane/EtOAc, 8:2, v/v), gave nitrone 21 (257 mg, 88%) as a white solid: mp 170-2° C.; IR (KBr) $v_{max}$ 2948, 1595, 1385, 1344, 1213 cm$^{-1}$; $^1$H NMR (400 MHz, CDCl$_3$) δ 10.10 (s, 1H, H-4), 8.05 (s, 1H, N=CH), 7.77 (ddd, J=7.9, 3.7, 1.2 Hz, 2H, H-6, H-7), 7.62 (ddd, J=8.4, 7.1, 1.5 Hz, 1H, H-5), 7.52 (dd, J=7.8, 1.7 Hz, 2H, Ph), 7.42 (m, 3H, Ph), 7.36 (ddd, J=8.2, 7.0, 1.2 Hz, 1H, H-8), 5.11 (s, 2H, CH$_2$), 4.10 (s, 3H, OCH$_3$); $^{13}$C NMR (101 MHz, CDCl$_3$) δ 158.7 (C, C-2), 146.5 (C, C-8a), 137.4 (CH, C-4), 133.5 (C, C-1'), 130.9 (CH, C-5), 129.3 (2CH-Ph), 129.3 (CH, C-4'), 129.2 (CH, C-6), 129.2 (2CH-Ph), 128.6 (CH, N=CH), 127.0 (CH, C-7), 125.3 (C, C-4a), 124.8 (CH, C-8), 115.3 (C, C-3a), 71.9 (CH$_2$), 54.0 (CH$_3$); MS (ESI) m/z: 293 [M+1]$^+$, 315 [M+Na]$^+$. Anal. Calcd. for C$_{18}$H$_{16}$N$_2$O$_2$: C, 73.95; H, 5.52; N, 9.58. Found: C, 73.66; H, 5.85; N, 9.28.

(Z)-1-(2-Chloro-6-methoxyquinolin-3-yl)-N-methylmethanimine oxide (22). Following the general procedure, reaction of commercial 2-chloro-6-methoxyquinoline-3-carbaldehyde (221 mg, 1 mmol), Na$_2$SO$_4$ (410 mg, 3 mmol), Et$_3$N (0.30 mL, 2 mmol), and N-methylhydroxylamine hydrochloride (125 mg, 1.5 mmol) in THF (15 mL), after 1 h, and column chromatography (hexane/EtOAc, 9:1, v/v), gave nitrone 22 (150 mg, 60%) as a white solid: mp 167-8° C.; IR (KBr) $v_{max}$ 3008, 1617, 1497, 1190 cm$^{-1}$; $^1$H NMR (400 MHz, CDCl$_3$) δ 10.18 (s, 1H, H-4), 8.02 (s, 1H, N=CH), 7.85 (d, J=9.2 Hz, 1H, H-5), 7.38 (dd, J=9.2, 2.8 Hz, 1H, H-7), 7.17 (d, J=2.8 Hz, 1H, H-8), 4.00 (s, 3H, NCH$_3$), 3.92 (s, 3H, OCH$_3$); $^{13}$C NMR (101 MHz, CDCl$_3$) δ 158.7 (C, C-2), 145.7 (C, C-6), 143.3 (C, C-8a), 136.2 (CH, C-4), 130.7 (CH, N=CH), 129.7 (CH, C-5), 128.3 (C, C-4a), 124.6 (CH, C-7), 122.6 (C, C-3), 106.5 (CH, C-8), 55.9 (OCH$_3$), 55.7 (NCH$_3$); MS (ESI) m/z: 251 [M+1]$^+$, 273 [M+Na]$^+$, 523 [2M+Na]$^+$. Anal. Calcd. for C$_{12}$H$_{11}$ClN$_2$O$_2$: 57.50; H, 4.42; N, 11.18. Found: C, 57.23; H, 4.80; N, 11.17.

(Z)—N-tert-Butyl-1-(2-chloro-6-methoxyquinolin-3-yl) methanimine oxide (23). Following the general procedure, reaction of commercial 2-chloro-6-methoxyquinoline-3-carbaldehyde (221 mg, 1 mmol), Na$_2$SO$_4$ (410 mg, 3 mmol), Et$_3$N (0.30 mL, 2 mmol), and N-(tert-butyl)hydroxylamine hydrochloride (188 mg, 1.5 mmol) in THF (15 mL), after 2.5 h, and column chromatography (hexane/EtOAc, 3:2, v/v), gave nitrone 23 (239 mg, 82%) as a pale yellow solid: mp 141-2° C.; IR (KBr) $v_{max}$ 2951, 1618, 1496, 1231, 1054 cm$^{-1}$; $^1$H NMR (400 MHz, CDCl$_3$) δ 10.26 (s, 1H, H-4), 8.23 (d, 1H, N=CH), 7.81 (d, J=9.2 Hz, 1H, H-5), 7.34 (dd, J=9.2, 2.8 Hz, 1H, H-7), 7.10 (d, J=2.8 Hz, 1H, H-8), 3.86 (s, 3H, CH$_3$), 1.64 (s, 9H, 3CH$_3$); $^{13}$C NMR (101 MHz, CDCl$_3$) δ 158.3 (C, C-2), 146.1 (C, C-8a), 142.7 (C, C-6), 135.6 (CH, C-4), 129.3 (CH, C-5), 128.1 (C, C-4a), 125.3 (CH, N=CH), 123.9 (CH, C-7), 122.7 (C, C-3), 106.2 (CH, C-8), 72.3 (C, C(CH$_3$)$_3$), 55.5 (OCH$_3$), 28.2 (3CH$_3$); MS (ESI) m/z: 293 [M+1]$^+$, 315 [M+Na]$^+$. Anal. Calcd. for C$_{15}$H$_{17}$ClN$_2$O$_2$: C, 61.54; H, 5.85; Cl, 12.11; N, 9.57. Found: C, 61.23; H, 5.99; Cl, 12.31; N, 9.23.

(Z)—N-Benzyl-1-(2-chloro-6-methoxyquinolin-3-yl) methanimine oxide (24). Following the general procedure, reaction of commercial 2-chloro-6-methoxyquinoline-3-carbaldehyde (221 mg, 1 mmol), Na$_2$SO$_4$ (410 mg, 3 mmol), Et$_3$N (0.30 mL, 2 mmol), and N-benzylhydroxylamine hydrochloride (239 mg, 1.5 mmol) in THF (15 mL), after 3 h, and column chromatography (hexane/EtOAc, 8:2, v/v), gave nitrone 24 (254 mg, 78%) as a white solid: mp 190-2° C.; IR (KBr) $v_{max}$ 3016, 1618, 1496, 1347, 1236 cm$^{-1}$; $^1$H NMR (300 MHz, CDCl$_3$) δ 10.18 (s, 1H, H-4), 8.09 (s, 1H, N=CH), 7.83 (d, J=9.2 Hz, 1H, H-5), 7.53 (m, 2H, Ph), 7.44 (m, 3H, Ph), 7.36 (dd, J=9.2, 2.8 Hz, 1H, H-7), 7.10 (d, J=2.6 Hz, 1H, H-8), 5.16 (s, 2H, CH$_2$), 3.89 (s, 3H, CH$_3$); $^{13}$C NMR (75 MHz, CDCl$_3$) δ 158.8, 143.4, 136.1, 133.1, 129.7, 129.6, 129.5, 129.4, 129.3, 128.4, 124.3, 122.7, 122.7, 106.7, 72.6, 55.8; MS (ESI) m/z: 327 [M+1]$^+$, 349 [M+Na]$^+$, 675 [2M+Na]$^+$. Anal. Calcd. for C$_{18}$H$_{15}$ClN$_2$O$_2$: C, 66.16; H, 4.63; N, 8.57. Found: C, 65.71; H, 4.63; N, 8.61.

(Z)—N-Benzyl-1-(2-chloro-6-hydroxyquinolin-3-yl) methanimine oxide (25). Following the general procedure, reaction of 2-chloro-6-hydroxyquinoline-3-carbaldehyde[51] (207 mg, 0.4 mmol), Na$_2$SO$_4$ (410 mg, 3 mmol), Et$_3$N (0.30 mL, 2 mmol), and N-benzylhydroxylamine hydrochloride (239 mg, 1.5 mmol) in THF (15 mL), after 1 h, and column chromatography (hexane/EtOAc, 1:1, v/v), gave nitrone 25 (187 mg, 60%) as a white solid: mp desc. ° C.; IR (KBr) $v_{max}$ 3083, 1616, 1472, 1174, 1049 cm$^{-1}$; $^1$H NMR (300 MHz, DMSO-d$_6$) δ 10.29 (s, 1H, OH), 9.98 (s, 1H, H-4), 8.44 (s, 1H, N=CH), 7.77 (dd, J=9.1, 1.7 Hz, 1H, H-5), 7.53 (m, 2H, Ph), 7.39 (m, 3H, Ph), 7.34 (t, J=2.4 Hz, 1H, H-7), 7.17 (t, J=2.3 Hz, 1H, H-8), 5.28 (s, 2H, CH$_2$); $^{13}$C NMR (101 MHz, DMSO) δ 157.3 (C, C-8a), 144.8 (C, C-2), 141.9 (C, C-6), 135.1 (C, C-1'), 134.9 (CH, C-4), 129.9 (2CH, Ph), 129.8 (CH, C-5), 129.2 (2CH, Ph), 128.6 (C, C-4a), 124.6

(CH, C-7), 123.2 (C, C-3), 110.0 (CH, C-8), 71.3 (CH$_2$); MS (ESI) m/z: 313 [M+1]$^+$, 335 [M+Na]$^+$, 553 [2M+1]$^+$, 647 [2M+Na]$^+$. Anal. Calcd. for C$_{17}$H$_{13}$ClN$_2$O$_2$: C, 65.29; H, 4.19; N, 8.96. Found: C, 64.98; H, 4.35; N, 8.99.

(Z)—N-Benzyl-1-(2,6-dichloroquinolin-3-yl)methanimine oxide (26). To a solution of 2,5-dichloroquinoline-3-carbaldehyde (78 mg, 0.35 mmol) and Na$_2$SO4 (99 mg, 0.7 mmol) in EtOH (5 mL), N-benzylamine hydrochloride was added (85 mg, 1.2 mmol) followed by Et$_3$N (0.10 mL, 2 mmol). After 16 h of reaction and column cromatography (hexane/EtOAc, 9:1, v/v), the nitrone 26 (65 mg, 56%) was obtained as a white solid: mp 167-170° C.; IR (KBr) v$_{max}$ 3654, 2922, 1557, 1482, 1337, 1181, 1050 cm$^{-1}$; $^1$H NMR (400 MHz, CDCl$_3$) δ 10.20 (s, 1H, H-4'), 8.10 (s, 1H, HC=N), 7.87 (d, J=8.9 Hz, 1H, H-8'), 7.81 (d, J=2.3 Hz, 1H, H-5'), 7.65 (dd, J=8.9, 2.3 Hz, 1H, H-7'), 7.58-7.30 (m, 5H, Ph), 5.17 (s, 2H, CH$_2$Ph). $^{13}$C NMR (101 MHz, CDCl$_3$) δ 148.7 (C-2', Ar), 145.4 (C-8a', Ar), 136.2 (C-4', Ar), 133.6, 132.7 (C-3', Ar), 132.6 (C-7', Ar), 129.9, 129.6, 129.4, 129.2 (C=N, 4Ph, C-8'), 127.9 (C-5', Ar), 127.7, 123.4, 72.7 (CH$_2$Ph); MS (ESI) m/z: 331.0 (M+H)$^+$. Anal. Calcd for C$_{17}$H$_{12}$Cl$_2$N$_2$O: C, 61.65; H, 3.65; N, 8.46. Found: C, 61.57; H, 3.94; N, 8.25.

(Z)—N-Benzyl-1-(2-chloro-7-methoxyquinolin-3-yl)methanimine oxide (27). Following the general procedure, reaction of commercial 2-chloro-7-methoxyquinoline-3-carbaldehyde (221 mg, 0.4 mmol), Na$_2$SO$_4$ (100 mg, 1 mmol), and N-benzylhydroxylamine hydrochloride (239 mg, 1.5 mmol) in EtOH (5 mL), after 3.5 h, and column chromatography (hexane/EtOAc, 8:2, v/v), gave nitrone 27 (98 mg, 30%) as a white solid: mp 170-1° C.; IR (KBr) v$_{max}$ 2955, 1616, 1454, 1348, 1228 cm$^{-1}$; $^1$H NMR (400 MHz, CDCl$_3$) δ 10.19 (s, 1H, H-4), 8.05 (s, 1H, N=CH), 7.71 (d, J=9.0 Hz, 1H, H-5), 7.51 (m, 2H, Ph), 7.42 (m, 3H, Ph), 7.26 (d, J=2.5 Hz, 1H, H-8), 7.17 (dd, J=9.0, 2.5 Hz, 1H, H-6), 5.12 (s, 2H, CH$_2$), 3.90 (s, 3H, CH$_3$); $^{13}$C NMR (101 MHz, CDCl$_3$) δ 162.9 (C, C-2), 149.3 (C, C8a), 149.0 (C, C-1'), 137.3 (CH, C-4), 133.0 (C, C-7), 130.3 (CH, C-5), 129.8 (CH, N=CH), 129.6 (2CH-Ph), 129.5 (CH, C-4'), 129.3 (2CH-Ph), 122.1 (C, C-4a), 120.9 (CH, C-8), 120.3 (C, C-3), 106.9 (CH, C-6), 72.2 (CH$_2$), 55.9 (CH$_3$); MS (ESI) m/z: 327 [M+1]$^+$, 349 [M+Na]$^+$, 653 [2M+1]$^+$, 675 [2M+Na]$^+$. Anal. Calcd. for C$_{23}$H$_{31}$ClN$_2$O$_4$Si: C, 59.66; H, 6.75; N, 6.05. Found: C, 59.74; H, 6.80; N, 5.95.

(Z)—N-Benzyl-1-(2-chloro-5,8-dimethoxyquinolin-3-yl)methanimine oxide (28). Following the general procedure, reaction of 2-chloro-5,8-dimethoxyquinoline-3-carbaldehyde[52] (251 mg, 1 mmol), Na$_2$SO$_4$ (410 mg, 3 mmol), Et$_3$N (0.30 mL, 2 mmol), and N-benzylhydroxylamine hydrochloride (239 mg, 1.5 mmol) in EtOH (10 mL), after 1.5 h, and column chromatography (hexane/EtOAc, 2:3, v/v), gave nitrone 28 (278 mg, 78%) as a yellow solid: mp 172-5° C.; IR (KBr) v$_{max}$ 2942, 1556, 1486, 1347 cm$^{-1}$; $^1$H NMR (400 MHz, CDCl$_3$) δ 10.50 (s, 1H, H-4), 8.11 (m, 1H, N=CH), 7.51 (m, 2H, Ph), 7.41 (m, 3H, Ph), 6.97 (d, J=8.6 Hz, 1H, H-7), 6.73 (d, J=8.6 Hz, 1H, H-6), 5.14 (s, 2H, CH$_2$), 3.97 (s, 3H, CH$_3$), 3.89 (s, 3H, CH$_3$); $^{13}$C NMR (101 MHz, CDCl$_3$) δ 149.8 (C, C-2), 148.3 (C, C-8a), 148.3 (C, C-5), 138.8 (C, C-8), 133.0 (C, C-1'), 132.8 (CH, C-4), 129.6 (2CH-Ph), 129.6 (CH, N=CH), 129.5 (CH, C-4'), 129.3 (2CH-Ph), 122.1 (C, C-4a), 120.4 (C, C-3), 110.3 (CH, C-7), 105.1 (CH, C-6), 72.4 (CH$_2$), 56.4 (CH$_3$), 56.0 (CH$_3$); MS (ESI) m/z: 357 [M+1]$^+$, 379 [M+Na]$^+$, 735 [2M+Na]$^+$. Anal. Calcd. for C$_{18}$H$_{15}$ClN$_2$O$_2$: C, 63.96; H, 4.80; Cl, 9.94; N, 7.85. Found: C, 64.05; H, 4.63; Cl, 10.06; N, 7.66.

(Z)—N-Benzyl-1-(2-chloro-6-methyl-1-oxidoquinolin-3-yl)methanimine oxide (29). Following the general procedure, reaction of 2-chloro-3-formyl-6-methylquinoline 1-oxide (221 mg, 1 mmol), Na$_2$SO$_4$ (410 mg, 3 mmol), Et$_3$N (0.30 mL, 2 mmol), and N-benzylhydroxylamine hydrochloride (239 mg, 1.5 mmol) in EtOH (10 mL), after 24 h at room temperature, and column chromatography (hexane/EtOAc, 1:1, v/v), gave (Z)—N-benzyl-1-(2-chloro-6-methyl-1-oxidoquinolin-3-yl)methanimine oxide (29) (192 mg, 59%) as a white solid: mp 163-165° C.; IR (KBr) v$_{max}$ 3430, 3075, 1556, 1455, 1335, 1208, 1065, 727 cm$^{-1}$; $^1$H NMR (400 MHz, CDCl$_3$) δ 9.79 (s, 1H, H-4), 8.55 (d, J=8.9 Hz, 1H, H-8), 7.99 (s, 1H, N=CH), 7.62 (s, 1H, H-5), 7.59 (d, J=8.9 Hz, 1H, H-7), 7.50 (m, 2H, 2CH-Ph), 7.43 (m, 3H, Ph), 5.15 (s, 2H, PhCH$_2$), 2.50 (s, 3H, CH$_3$); $^{13}$C NMR (100 MHz, CDCl$_3$) δ 140.5 (C8a), 139.8 (C6), 136.2 (C2), 134.3 (CH, C7), 132.6 (C1'), 129.6 (CH, C4'), 129.5 (2CH, C3', C5'), 129.3 (2CH, C2', C6'), 128.6 (CH, C5), 128.3 (C4a), 127.8 (N=CH), 125.0 (CH, C4), 123.3 (C3), 119.7 (CH, C8), 72.7, 21.5; MS (ESI) m/z: 349 [M+Na$^+$], 675 [2M+Na$^+$]; HRMS: Calcd for C$_{18}$H$_{15}$ClN$_2$O$_2$: 326.0809. Found: 326.0822.

(Z)—N-tert-Butyl-1-(2-chloro-6-methyl-1-oxidoquinolin-3-yl)methanimine oxide (30). Following the general procedure, reaction of 2-chloro-3-formyl-6-methylquinoline 1-oxide (221 mg, 1 mmol), Na$_2$SO$_4$ (410 mg, 3 mmol), Et$_3$N (0.30 mL, 2 mmol), and and N-(tert-butyl)hydroxylamine hydrochloride (188 mg, 1.5 mmol) in EtOH (10 mL), after 24 h at room temperature, and column chromatography (hexane/EtOAc, 3:2, v/v), gave (Z)—N-tert-butyl-1-(2-chloro-6-methyl-1-oxidoquinolin-3-yl)methanimine oxide (30) (198 mg, 68%) as a white solid: mp 211-214° C.; IR (KBr) v$_{max}$ 3421, 2966, 2232, 1670, 1553 cm$^{-1}$; $^1$H NMR (400 MHz, CDCl$_3$) δ 9.93 (s, 1H, H-4), 8.60 (br s, 1H, NH), 8.17 (d, J=8.9 Hz, 1H, H-8), 8.17 (s, 1H, N=CH), 7.66 (s, 1H, H-5), 7.62 (dd, J=8.9, 1.4 Hz, 1H, H-7), 2.53 (s, 3H, CH$_3$), 1.67 (s, 9H, 3CH$_3$); $^{13}$C NMR (75 MHz, CDCl$_3$) δ 140.5 (C8a), 139.8 (C6), 136.8 (C2), 134.1 (CH, C7), 128.6 (CH, C5), 128.0 (C4a), 124.9 (CH, C4), 124.4 (N=CH), 123.9 (C3), 119.8 (CH, C8), 73.3 (C(CH$_3$)$_3$), 28.5 (3CH$_3$), 21.7 (CH$_3$); MS (ESI) m/z: 315 [M+Na$^+$], 607 [2M+Na$^+$]. HRMS: Calcd for C$_{15}$H$_{17}$ClN$_2$O$_2$: 292.0976. Found: 292.0978.

(Z)—N-tert-Butyl-1-(tetrazolo[1,5-a]quinolin-4-yl)methanimine oxide (31). Following the general procedure, reaction of tetrazolo[1,5-a]quinoline-4-carbaldehyde[53] (100 mg, 0.5 mmol), Na$_2$SO$_4$ (300 mg, 1.5 mmol), Et$_3$N (0.20 mL, 1 mmol), and N-(tert-butyl)hydroxylamine hydrochloride (100 mg, 0.75 mmol) in EtOH (5 mL), after 15 h, and column chromatography (hexane/EtOAc, 1:1, v/v), gave nitrone 31 (97 mg, 72%) as a white solid: mp 207-209° C.; IR (KBr) v$_{max}$ 2975, 1553, 1522, 1138 cm$^{-1}$; $^1$H NMR (400 MHz, CDCl$_3$) δ 10.13 (s, 1H, H-4), 8.64 (d, J=8.7 Hz, 1H, H-5), 8.63 (s, 1H, N=CH), 8.03 (d, J=7.2 Hz, 1H, H-8), 7.87 (td, J=8.7, 7.2, 1.4 Hz, 1H, H-6), 7.71 (ddd, J=8.7, 7.2, 1.4 Hz, 1H, H-7), 1.71 (s, 9H, 3CH$_3$); $^{13}$C NMR (101 MHz, CDCl$_3$) δ 147.3 (C, C-8a), 132.0 (CH, C-5), 130.9 (C, C-3a), 130.8 (CH, C-8), 130.5 (CH, N=CH), 128.8 (CH, C-6), 125.1 (C, C-5a), 123.6 (CH, C-7), 117.1 (CH, C-9), 116.5 (C, C-4), 73.1 (C, C(CH$_3$)$_3$), 28.7 (3CH$_3$); MS (ESI) m/z: 270 [M+1]$^+$, 292 [M+Na]$^+$. Anal. Calcd. for C$_{14}$H$_{15}$N$_5$O: C, 62.44; H, 5.61; N, 26.01. Found: C, 62.05; H, 6.02; N, 25.97.

Estimation of Lipophilicity as C log P. Bioloom of Biobyte Corp was used for the theoretical calculation of lipophilicity as C log P values (BioByte Home Page. Available online: http://www.biobyte.com).

Interaction of the nitrone with the Stable Radical 1,1-diphenyl-picrylhydrazyl (DPPH) To a solution of DPPH in absolute ethanol the appropriate volume of the compounds (0.1 mM final concentrations) dissolved in DMSO was added. The absorbance was recorded at 517 nm after 20 and 60 min at room temperature (Table 1).

Hydroxyl Radicals Scavenging Activity.[32] The hydroxyl radicals were produced by the $Fe^{3+}$/ascorbic acid system. EDTA (0.1 mM), $Fe^{3+}$ (167 μM), DMSO (33 mM) in phosphate buffer (50 mM, pH 7.4), the tested compounds (0.1 mM) and ascorbic acid (10 mM) were mixed in test tubes. The solutions were incubated at 37° C. for 30 min. The reaction was stopped by trichloroacetic acid (17% w/v) (Table 1) and the % scavenging activity of the tested compounds for hydroxyl radicals was given.

Inhibition of Linoleic Acid Peroxidation.[32] For initiating the free radical, 2,2'-azobis(2-amidinopropane) dihydrochloride (AAPH) is used. The final solution in the UV cuvette consisted of ten microliters of the 16 mM linoleate sodium dispersion 0.93 mL of 0.05 M phosphate buffer, pH 7.4, thermostatted at 37° C. 50 μL of 40 mM AAPH solution was added as a free radical initiator at 37° C. under air and 10 μL of the tested compounds. The oxidation of linoleic acid sodium salt results a conjugated diene hydroperoxide. The reaction is monitored at 234 nm (Table 1).

ABTS$^{•+}$-decolorization assay in ethanolic solution for antioxidant activity.[32,35] ABTS is dissolved in water to a 2 mM concentration. ABTS radical cation (ABTS$^{•+}$) is produced by reacting the ABTS stock solution with 0.17 mM potassium persulfate in phosphate buffer (pH 7.4, 20 mM) and allowing the mixture to stand in the dark at room temperature for 12-16 h before use. For steady state measurements, 100 mM ABTS$^{•+}$ was used. For the present study, the 100 mM ABTS$^{•}$ solution (200 μL) was diluted with ethanol (790 μL) to an absorbance of 0.70 at 734 nm, equilibrated at room temperature, mixed with 10 μL of the tested compounds (stock solutions 10 mM) and the absorbance reading was taken at room temperature 1 min after the initial mixing. Trolox was used as a standard.

Inhibition of the Carrageenan-induced edema. Edema was induced in the right hind paw of Fisher 344 rats (150-200 g) by the intradermal injection of 0.1 mL 2% Carrageenan in water. Both sexes were used. Females pregnant were excluded. Each group was composed of 6 animals. The experiment was performed twice for validation. The animals, which have been bred in our laboratory, were housed under standard conditions and received a diet of commercial food pellets and water ad libitum during the maintenance, but they were entirely fasted during the experiment period. Nitrone 23 as well as of the standard drug indomethacin in 0.01 mmol/kg body weight, were diluted in water with few drops of Tween 80 and ground in a mortar before use and they were given intraperitoneally simultaneously with the Carrageenan injection. The rats were euthanized 3.5 h after Carrageenan administration. The difference between the weight of the injected and uninjected paws was calculated for each animal. The change in paw weight was compared with that in control animals (treated with water/or Tween-water) and expressed as a percent inhibition of the edema % ICPE values (Table 2). Values % ICPE are the mean from two different experiments (n=6 animals each time) with a standard error of the mean less than 10%.

Quantitative nitrite assays for NO release. A solution of nitrone 23 (final concentration 100 μM) (20 μL), dissolved in DMSO, was added to 2 mL of 50 mM phosphate buffer (pH=7.4) containing the appropriate amount of thiol cofactor 1 mM (L-cysteine). After 60 min at 37° C., 1 mL of the reaction mixture was treated with 250 μL of the Griess reagent (4 g sulfanilamide, 0.2 g N-naphthyl-ethyldiamine dihydrochloride, 10 mL of 85% phosphoric acid in distilled water, final volume 100 mL). After the mixture stood for 10 min at rt, absorbance was recorded at 540 nm. Sodium nitroprusside (SNP) was used as standard reference compound (100 μM). The yield in nitrite ($NO_2^-$ release) for nitrone 23, as function of L-cysteine (mM concentration) is given in Table 1, expressed as % $NO_2^-$ (mol/mol).

Primary neuronal cultures. Primary neuronal cultures from rat cerebral cortex were prepared as previously described.[54] All procedures associated with animal experiments were approved by the Ethics Committee of the Hospital Ramón y Cajal, Madrid (Spain). Cell suspensions from cerebral cortex were prepared from 16- to 17-day-old Sprague-Dawley rat embryos. Living cells in cell suspension were counted by trypan blue exclusion method. Cells were seeded on plastic multidishes precoated with 0.05 mg/mL poly-D-lysine at a density of $2.5 \times 10^5$ cells/$cm^2$ and were kept at 37° C. in a 6.5% $CO_2$ atmosphere in high glucose Dulbecco's medium supplemented with 15% heat-inactivated (56° C. for 30 min) foetal calf serum. After 24 h, cultured cells were placed in, and maintained in, serum-free glucose deprivation (OGD) to induce experimental ischemia.[23] Cultured cells were washed and placed in glucose-free Dulbecco's medium (bubbled with 95% $N_2$/5% $CO_2$ for 30 min), and maintained in a humidified hypoxia chamber equipped with an oxygen and carbon dioxide control unit (Biospherix) at 6.5% $CO_2$ and <0.1% $O_2$ in $N_2$ at 37° C. Cells were exposed to OGD for a period of 4 h (OGD 4 h). At the end of the OGD period, culture medium was replaced with oxygenated serum-free medium, and cells were placed and maintained in the normoxic incubator for 24 h to recovery (R24 h). In the neuroprotection experiments, the compounds were added at the onset of recovery period. Control cultures in Dulbecco's medium containing glucose were kept in the normoxic incubator for the same period of time as the OGD, and then medium (Dulbecco's/Ham's F12, 1:1 [vol/vol], 5 mg/mL glucose, 2 mM L-glutamine, and 1 mM sodium pyruvate, and supplemented with 100 μg/mL transferrin, 100 μM putrescine, 20 nM progesterone, 30 nM sodium selenite and 5 μg/mL insulin). Here, 6-7 day old cultured neurons were used in the experiments, and contained 90% β-III-tubulin-positive mature neurons, as described previously.[55]

Exposure of cell cultures to oxygen-glucose deprivation and treatments. Primary neuronal cultures were exposed to oxygen-culture medium was replaced with serum-free medium and cells were returned to the normoxic incubator until the end of recovery period. Control experiments included the same amounts of vehicle (final concentration<0.5% ethanol). Nitrone 2 was used as reference compound for neuroprotection. The experimental procedures were blindly performed, assigning a random order to each assayed nitrone. Nitrones were analyzed independently four-eight times with different batch of cultures and each experiment was run in quadruplicate.

Cell viability assay. Cell viability was evaluated by quantification of living, metabolically active cells, as determined by a colorimetric assay using the photometric reduction of 3-(4,5-dimethylthiazol-2-yl)-2,5-diphenyl tetrazolium bromide (MTT) (Roche) to a blue formazan product. The assay of living, metabolically active cells was performed by incubating with 0.2 mg/mL MTT in the culture medium for 1.5 h in an incubator at 37° C. in a 6.5% $CO_2$ atm. After the incubation period, cells were lysed with an equal volume of 10 mM HCl and 10% SDS overnight. Values were quantified by absorbance (test 595 nm, reference 690 nm). Decreased MTT activity denotes impairment of mitochondrial function and is considered to be an index of cell damage. Primary neuronal cultures were collected at times indicated for MTT determination.

Measurement of the ROS formation. To detect the intracellular ROS formation a nonfluorescent and cell permeable reagent was used according to the supplier instructions (Sigma, MAK143). The reagent enters into the cells and reacts with ROS (especially superoxide and hydroxyl radicals) in the cytoplasm, resulting in a fluorometric product proportional to the amount of ROS present. The reagent was added to the cells at the moment that they were subjected to different treatments. After recovery period for 2 h, the fluorescence intensity was at 490 nm $\lambda_{ex}$ and 535 nm $\lambda_{em}$.

Lipid peroxidation. Lipid peroxidation was evaluated by the detection of end products such as malondialdehyde (MDA) as a result of oxidative attack to polyunsaturated lipids. Lipid peroxidation was determined by the reaction of MDA with thiobarbituric acid (TBA) to form a colorimetric/fluorometric product, proportional to the MDA present. After recovery period for 4 h, cells ($1.5 \times 10^6$) were lysed and centrifuged according to the supplier instructions (Sigma, MAK085), and then the thiobarbituric acid was added to the supernatant and mixed in a vortex. The samples were incubated at 95° C. for 60 min, cooled to room temperature and then n-butanol and 5M NaCl were added in a reaction mixture 8:3:1 (v/v) sample:n-butanol:NaCl. After mixed in a vortex, the samples were centrifuged, the n-butanol layer was taken and evaporated, the MDA-TBA adducts were dissolve in water and the absorbance was measured at 540 nm.

Animal model of global cerebral ischemia, experimental design and administration of nitrones. Transient forebrain ischemia was induced in adult male Wistar rats (10-12 weeks, Charles River) by the standard four-vessel occlusion model (4VO) previously described.[44,56] Briefly, both vertebral arteries were irreversibly occluded by electrocoagulation under anesthesia with a mixture of atropine, ketamine and diazepam (0.25, 62.5, and 5 mg/kg, respectively) delivered by intraperitoneal injection. After 24 h, ischemia was induced by carotid occlusion with atraumatic clips for 15 min and then clips were removed from the carotid arteries to allow reperfusion. Body temperature of 37° C. was maintained. The animals were studied after 5 days of reperfusion (R5 d). We performed a power analysis (http://www.biomath.info/power/ttest.htm) to determine the sample size. We chose the significant level at 0.05, the power set at 0.8 (80%), and a ratio of control/treated group of 2:1, and the sample size obtained was 10 subjects per control group and <6 subjects per treated group. A total of 26 ischemic animals were used for the study of nitrone 23 efficacy. Here 6 animals were treated with 1.5 mg/kg of nitrone 23, or 40 mg/kg of compound 2, and 14 animals were included in control (vehicle) group, two of which died after 2 days. The treatments were performed with allocated concealment, assigning a random order to each vehicle or treated animal by computer-generated randomization program. Ischemic animals were treated with nitrone 23 diluted in 10% ethanol in saline as vehicle by intraperitoneal injection when the carotid arteries were unclamped for reperfusion. Vehicle-treated control animals were prepared in the same way as the treated animals. An independent investigator prepared the treatments for each animal according to the randomization schedule. All procedures associated with animal experiments were approved by The Ethics Committee of the Hospital Ramon y Cajal, Madrid, Spain, and performed according to ARRIVE guidelines.

Evaluation of neurological deficits. Neurological deficits in rats subjected to global cerebral ischemia were blindly evaluated using a scale previously described in Ayuso et al.[22] Evaluation of the overall neurological deficit score (NDS), including a score of general deficit and subscores in movement and sensory assessment, range from 0 (best) to 10 (rats had a depressed level of consciousness) and was validated in an entire cohort of R5 d animals (n=20) (see ref 22 for details).

Brain sections. After 5-days reperfusion, R5 d animals were killed by transcardiac perfusion performed under deep anesthesia. Perfusion via left ventricle was started with a washout of 200 ml, of 0.9% NaCl, and the brains, following perfusion and fixing with 4% (w/v) paraformaldehyde solution in PBS, were removed and postfixed in the same solution overnight at 4° C. Brains were washed sequentially with 10, 20 and 30% (w/v) saccharose in PBS, embedded in Tissue-Tek O.C.T. (Sakura Finetek) and frozen at −80° C. prior to cryostat sectioning. Brain coronal sections containing the hippocampus were prepared at the level of interaural+5.7±0.2 mm on Real Capillary Gap microscope slides (Dako).

Neuronal death evaluation. Neuronal death was evaluated by Fluoro-Jade-B staining. Brain cryosections (10 μm thick) from ischemic animals that underwent reperfusion for 5 days were used after fixation to detect neuronal death by Fluoro-Jade-B staining,[44] and visualized by fluorescence microscopy. Labeled (dead) neuronal cells (in green) were counted as in TUNEL assay (see below). Data from different animals of each experimental group were independently analyzed by two observers, and treatment information was blindly performed throughout the study.

TUNEL assay. Apoptotic neurons within brain sections were detected using the Terminal deoxynucleotidyl transferase-mediated dUTP Nick-End Labeling (TUNEL) assay (Promega). Coronal cryotome brain sections containing the dorsal hippocampal formation were cut at 5 ilm as described above. Sections were postfixed with 4% formaldehyde in PBS for 20 min and permeabilized with 20 μg/mL proteinase K in PBS for 10 min at room temperature, washed in PBS and a terminal deoxynucleotidyl transferase (TdT) incubation was carried out for 1.5 h at 37° C. with fluorescein-12-dUTP as described by the supplier. The reaction was terminated by extensive washing in PBS and deionized water at room temperature. A positive control was performed by nicking the nuclear DNA with DNase I as specified by the supplier. A negative control was achieved by excluding the TdT enzyme from the reaction. The sections were then mounted with coverslips in antifade solution with glycerol-buffer containing p-phenylenediamine and 30 μM bisbenzimide (Hoechst 33342) for nuclear staining.

The hippocampal CA1 subfield and cerebral and lateral cortex fields from a given section were analyzed with fluorescence microscopy (40× objective) to count the number of apoptotic nuclei (green). A grid of 330×220 μm² was used to count the cells in the regions of interest and digitized with a color CCD camera (1280×960 pixel resolution). TUNEL-positive cells were counted by two independent observers with a total area of 1.017 mm² per section analyzed. Four sections per brain sample were averaged per experiment and treatment information was kept concealed throughout the study.

Animal model of focal cerebral ischemia. Transient occlusion of a distal branch of the middle cerebral artery (tMCAO) was induced in male C57BL/6 mice (9-12 week old, Charles River) as previously described.[57] The animals were housed in a light/dark cycle (12 hour), humidity and temperature (22±2° C.) controlled environment with food and water available ad libitum. Briefly, mice were anesthetized with 4% isoflurane for induction and 1.5-2% isoflurane for maintenance (in 79% N2/21% O2). After drilling a small hole on the temporal bone, the middle cerebral artery (MCA) was compressed for 60 min with a 30-G needle using a micromanipulator. During the surgery, body temperature was maintained between 37.0±0.5° C. using a homoeothermic blanket and CBF was monitored using laser-Doppler flowmetry to confirm MCA occlusion. Buprenorphine (0.05-0.1 mg/kg) was administered subcutaneously immediately before the procedure. A total of 28 mice were subjected to tMCAO according to the design of the study. We performed a power analysis to determine sample size (significance level set at 0.05, the power set at 0.8 (80%)) resulting in 8 animals per experimental group. Surgical inclusion criteria: a reduction in blood flow to <25% of baseline value during ischemia period, and a recovery of 75% of baseline value in the reperfusion period. Animals that met the following criteria were excluded: (i) Animals that failed to meet the inclusion criteria explained above (2 mice); and (ii) death during the induction of middle cerebral artery occlusion (MCAO) (2 mice). Mice were randomly assigned using a randomization software to the following experimental groups (n=8 per group): vehicle (saline-EtOH 90:10 vol/vol), nitrone 23 (1.5 mg/kg) and nitrone 23 (2.0 mg/kg). The treatments were administered intraperitoneally at the onset of reperfusion period by a blinded investigator. All procedures were approved by the local Animal Care Committee and were conducted in compliance with ARRIVE guidelines and the Spanish legislation and in accordance with the Directives of the EU.

Motor-deficit evaluation, grip strength test. Motor functional test was performed at 1 day before surgery and 24 h and 48 h after tMCAO to evaluate ischemic outcomes and monitor motor function by a blinded researcher to experimental conditions. Grip strength test is designed to assess the maximum force displayed by the mouse forelimbs (in grams) using a metallic grid connected to a force sensor (Bioseb). A total of 6 trials were conducted for each test and the strength value was calculated as the mean of them.

Infarct volume evaluation. The size of infarction was evaluated at 48 hours after MCAO using 2,3,5-tetrazolium chloride (TTC) staining.[58] Mice were sacrificed by transcardial perfusion with ice-cold saline under deep anesthesia. Brains were removed and cut into 1-mm-thick coronal sections and stained with 2.5% of TTC in saline for 20 min at room temperature. We performed all analysis in a blinded manner. The infarct areas were measured using the Image-J software and the infarct volume was determined by linear integration of the measured lesion areas and distances over the sections. In order to avoid the brain edema effects, infarct area was corrected by the ratio of the area of the ipsilateral and the contralateral hemisphere.

Statistical analysis. Data from each treatment and the different animals from each experimental condition or group were independently analyzed and their averaged values were used for statistical analysis. The treatment information was kept concealed throughout the study. Data were expressed as mean±SE. Analysis of variance (ANOVA) was performed to compare the data between multiple concentrations or groups, following post hoc test when analysis of variance was significant. Statistical significance was set at $p<0.05$ using Prism statistical software (GraphPad Software).

1. Chemistry

Known or not previously described, unsaturated nitrogenated derivatives 5, 6, 7, 8, 9 and 10 (FIG. 2A) have been synthesized by reaction of commercial 2-chloro-6-methylquinoline-3-carbaldehyde with hydroxylamine, hydrazine, O-benzylhydroxylamine, N-benzylhydrazine, N-benzylamine and t-butylamine, respectively, by the usual protocols (see Materials and methods).

Scheme 1. Synthesis of nitrones 11-31.

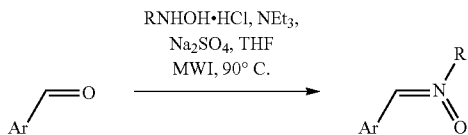

Figure 3:
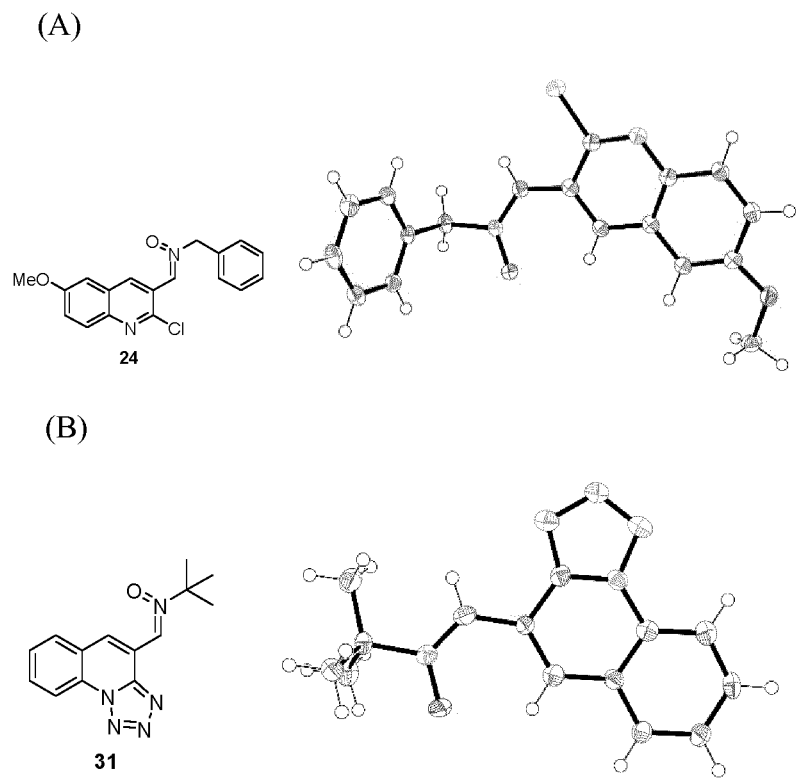
FIG. 3. ORTEP images of QNs 24 (A) and 31 (B). Ellipsoids are drawn at 50% probability level.

Nitrones 11-31 (FIG. 2 A-D) have been obtained according to the general procedure shown in Scheme 1, from the corresponding commercially available carbaldehyde, and N-methyl, N-t-butyl or N-benzylhydroxylamine hydrochloride (see Materials and methods). All new compounds have been characterized by their analytical and spectroscopic data (see Materials and methods). In the case of the QNs, the stereochemistry at the double bond has been assigned as Z by comparing NMR data with those analyzed and reported for known nitrones. Structure of nitrones 24 and 31 has been confirmed by X-ray diffraction analysis (FIG. 3).

2. Neuroprotection Evaluation Against Experimental Ischemia in Neuronal Cultures Neuroprotection of compounds was evaluated by a cell viability assay. The neuroprotective effect of the compounds 5-32 was evaluated on primary neuronal cultures from cerebral cortex subjected to oxygen-glucose deprivation (OGD) to induce experimental ischemia. Afterwards, cultured neurons were placed and kept in normoxic and normoglycemic conditions to recovery. Cell viability assay by 3-(4,5-dimethylthiazol-2-yl)-2,5-diphenyl tetrazolium bromide (MTT) determination was performed in the recovery period after OGD to evaluate the potential neuroprotective effect on the compounds investigated against experimental ischemia. Exposure of neuronal cultures to 4 h OGD (OGD4 h) induced a significant decrease in cell viability (67.6%, $p<0.0001$ compared with 100% control, by one-sample t test), which was partially reversed after 24 h of recovery (R24 h, 77.1%; $p<0.001$ compared with OGD 4 h, Student's t test), but without reaching the 24 h control value ($p<0.0001$ compared with 100% control, one-sample t test) (FIG. 4).

The unsaturated azo compounds 5-10, the new nitrones 11-31, the compound 32 (FIG. 2), as well as the well-known neuroprotective nitrone 2 (NXY-059, FIG. 1)—used here as reference nitrone to evaluate the neuroprotection on neuronal cultures—and our previously reported nitrone 4 (FIG. 1)—used here for comparative purposes—, were added at the beginning of the recovery period to evaluate their potential neuroprotective effect after 24 h of recovery.

Figure 4:
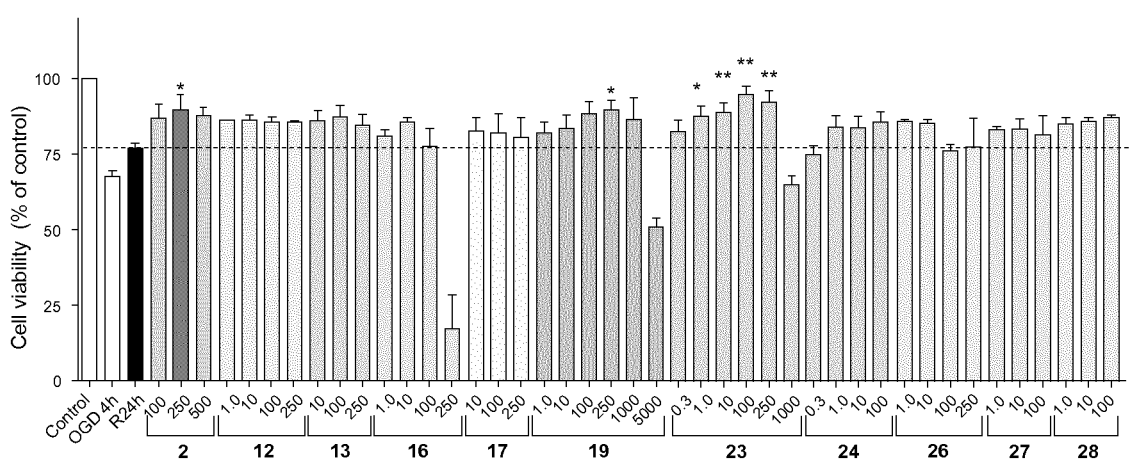
FIG. 4. Effect of QNs on primary neuronal cultures exposed to oxygen glucose deprivation (OGD). Bar chart showing the percentage of cell viability at 24 h of recovery after 4 h OGD, either untreated (R24 h) or treated with different concentrations (μM) of QNs 2, 12, 13, 16, 17, 19, 23, 24, or 26-28. The value induced by OGD at 4 h without recovery period (OGD 4 h) is also indicated. Cell viability corresponding to control cells (1.281±0.08 AU) was considered as 100%. The values represent the average of four to eight independent experiments; error bars representing the SE. *$P<0.05$, and **$P<0.01$ compared with R24 h (dotted line) by Dunnett's post test after ANOVA, when it was significant. Statistical significances for cell viabilities values lower than R24 h value were not shown. The results of other studied nitrones are shown in FIG. 11.

Reference nitrone 2, assayed from 1 μM to 1 mM, only produced a significant neuroprotective effect at 250 μM (FIG. 4). The addition of nitrone 19 (250 μM), or nitrone 23 (1-250 μM), significantly increased neuronal viability compared with R24 h, being near control value at 100 μM concentration (FIG. 4). Conversely, nitrones 12, 13, 16, 17, 24, and 26-28, increased neuronal viability at the indicated concentrations in FIG. 4, but without statistical significance compared with R24 h. Nitrones 11, 14, 15, 18, 20-22, 25, and 31, showed no increase in neuronal viability.

From these results, interesting and useful SAR have been observed. First of all, and very interestingly, neither the unsaturated azo compounds 5-10, nor carbaldehyde 32, the precursor of potent QN 23, showed neuroprotective activity. This result confirms the higher neuroprotection of nitrones compared to related oximes (compounds 5, 6), hydrazones (compounds 7, 8) and imines (compounds 9, 10), or the parent carbaldehyde precursor (32).

Regarding the group attached to the nitrone moiety, the incorporation of a phenyl motif (compound 11, FIG. 2A), instead of a t-butyl (compound 3, FIG. 1) or a benzyl group (compound 4, FIG. 1) seems deleterious for the neuroprotective activity of the resulting QN. Similar observation can be made when a methyl group is the one implemented at the nitrone moiety (compare nitrone 22 with compounds 23 and 24, FIG. 2C).

For t-butyl nitrones 17-19, 23 and 31, the combination of functional groups MeO(C6)/Cl(C2) as shown in compound 23 gives better neuroprotection power than the no substitution at ring A/OH(C2) (compound 19) or the combination of functional groups Me(C6)/OH(C2) as shown in compound 17, and higher neuroprotection power than the no substitution at ring A/Cl(C2) (compound 18). The incorporation of a fused tetrazole ring onto the quinoline core, as in nitrone 31, gives no improvement for the neuroprotection compared with nitrones 18 or 19.

Among the benzyl nitrones 12-16, 20, 21 and 24-28, the most potent, taking into account the mean values at the different dose concentrations, were compounds 12, 13, 16, 17, 19, 24 and 26-28 (FIG. 4), but none of them showed a clear better or higher neuroprotection than the others. This means that for benzyl nitrones, as shown before for t-butyl nitrones, no clear SAR can be defined, and a diverse array of functional group combination can afford good neuroprotection. Thus, regardless of the type, position or number of the groups in the ring A, and at C2, a quite similar neuroprotective effect was observed for QNs 24, 27 and 28.

Surprisingly, Me(C6)nitrones 14 and 15, bearing a MeO and a NHMe at C2, respectively, were less potent than those bearing no substituent (12), OH (13) or NMe$_2$ (16) at C2. Comparing Cl(C2)nitrones 25 and 26, the one bearing a Cl(C6) showed a better neuroprotective profile than the one bearing a OH(C6). Both no substituted nitrones at ring A, bearing a Cl atom (20) or a MeO (21) at C2, were poor neuroprotective compounds.

To sum up, we conclude that preferred functional groups leading to efficient neuroprotective activities are: (a) the nitrone group is effectively better than non-nitrone precursors or derivatives; (b) t-butyl or benzyl group at the nitrone moiety; (c) for t-butyl (or benzyl) nitrones, we have not found clear SAR, but a potent electron donor group at C6, such as the MeO with a Cl atom at C2 seems to afford the best neuroprotective effect.

Finally, we defined neuroprotection activity as the percentage from R24 h value, defined as 0%, to reach the control value, as 100% (Table 1). The neuroprotection induced by QNs 19 and 23 was compared with that induced by reference compounds 2, (250 µM) and 4 (50 µM). Particularly, we found that the most potent neuroprotective agent was nitrone 23 (100-250 µM), providing a very significantly higher neuroprotection than QNs 2 and 4 (Table 1). Among the compounds investigated, we did not find neuroprotection values higher than the reference nitrones 2 and 4, and new quinolylnitrones 19 and 23 (Table 1).

TABLE 1

Neuroprotective activity for selected QNs in neuronal cultures exposed to oxygen-glucose deprivation (OGD) [a]

| Nitrone | Concentration (µM) | Neuroprotection (%) |
|---|---|---|
| 2 | 250 | 52.90 ± 2.52 |
| 4 | 10 | 55.38 ± 1.74 |
|   | 50 | 56.82 ± 2.57 |
| 19 | 100 | 48.76 ± 2.29 |
|   | 250 | 55.00 ± 1.89 |
| 23 | 10 | 52.03 ± 1.75 |
|   | 100 | 77.08 ± 2.24 *** |
|   | 250 | 65.88 ± 2.87 * |

[a] Neuroprotection was defined as the percentage to reach the control value (defined as 100%) from R24 h value (defined as 0%).
* $p < 0.05$,
*** $p < 0.001$, compared with both QN 2 and 4 (50 µM), by Newman-Keuls post test after ANOVA.
Data represented as mean ± SE.

Due to the good neuroprotective profile of QN 23 (FIG. 2C), next we carried out the analysis of its antioxidant capacity on several selected and specific experiments to determine its ability to scavenge and trap different types of ROS.

3. Antioxidant Evaluation of QN 23

The formation of ROS is an unavoidable event for aerobic organisms, as a consequence of their cell metabolism. The involvement of these reactive species in the ischemia-related damage in myocardial and the central nervous system (CNS) is under intensive study. Due to the extreme reactivity and tendency of ROS to initiate and participate in chain reactions, the role of antioxidants as a defense system is highly recognized. Antioxidants are defined as substances that, even at low concentration, significantly delay or prevent oxidation of easily oxidizable substrates and therefore seem adequate in the fight against oxidative stress.

We performed an in vitro antioxidant profile evaluation of QN23 and other selected QNs, in order to characterize and compare its antioxidant capacity in vitro, and to find a possible relationship between the radical scavenging properties and the neuroprotection observed in OGD experiments. Together with QN23, we selected two QNs (19, 24) with intermediate neuroprotective effect and two QNs (18, 22) with low neuroprotective effect against OGD (FIG. 4 and 1S (SI), respectively), in addition to the reference nitrone 2. The results are shown in Table 3 below.

TABLE 2

In vitro antioxidant activity of QN 23

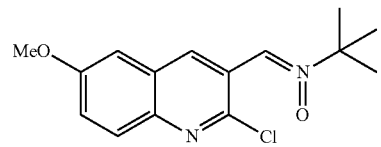 [SMILES: COc1ccc2nc(Cl)c(/C=[N+](\[O-])C(C)(C)C)cc2c1]

| QN | LOX (%) | AAPH (%) | DPPH (%) | *OH (%) | ABTS*+ (%) | (%) NO$_2^-$ (mol/mol) |
|---|---|---|---|---|---|---|
| 23 | 29 | 22 | 4 | 100 | 7 | 3 |
| NDGA | 87 |   | 93 |   |   |   |
| Trolox |   | 63 |   | 73 | 91 |   |
| SNP |   |   |   |   |   | 58 |

Values are means ± SD of three or four different determinations. Means within each column differ significantly ($p < 0.05$).

TABLE 3

In vitro antioxidant activity of QNs 18, 19, 22, 23 and 24, nitrone 2 (NXY-059) and standard reference compounds caffeic acid, NDGA, Trolox and SNP

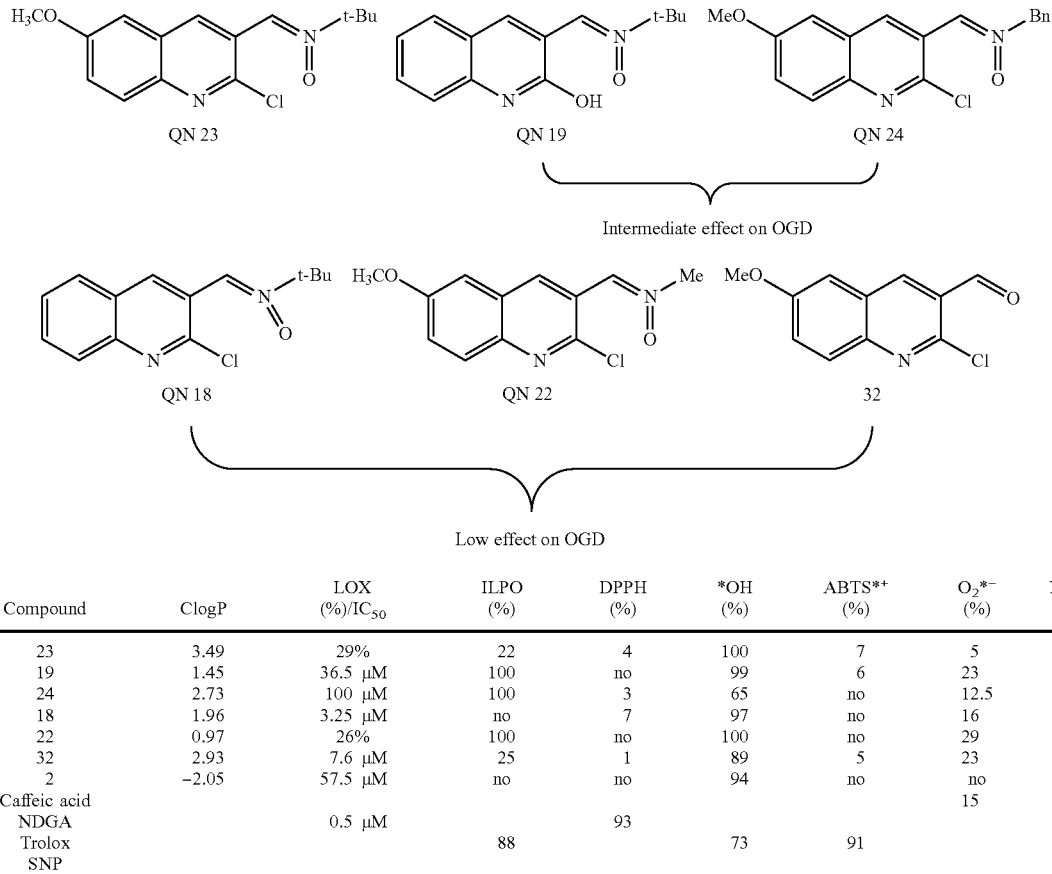

| Compound | ClogP | LOX (%)/IC$_{50}$ | ILPO (%) | DPPH (%) | *OH (%) | ABTS*+ (%) | O$_2$*− (%) | NO$_2^-$ (%)* |
|---|---|---|---|---|---|---|---|---|
| 23 | 3.49 | 29% | 22 | 4 | 100 | 7 | 5 | 3 |
| 19 | 1.45 | 36.5 μM | 100 | no | 99 | 6 | 23 | * |
| 24 | 2.73 | 100 μM | 100 | 3 | 65 | no | 12.5 | 12.5 |
| 18 | 1.96 | 3.25 μM | no | 7 | 97 | no | 16 | 7.5 |
| 22 | 0.97 | 26% | 100 | no | 100 | no | 29 | 11 |
| 32 | 2.93 | 7.6 μM | 25 | 1 | 89 | 5 | 23 | 2.5 |
| 2 | −2.05 | 57.5 μM | no | no | 94 | no | no | 1 |
| Caffeic acid | | | | | | | 15 | |
| NDGA | | 0.5 μM | | 93 | | | | |
| Trolox | | | 88 | | 73 | 91 | | |
| SNP | | | | | | | | 58 |

Values are means of three to four different determinations. Means within each column differ significantly (p < 0.05) compared with the reference compound Nitrones tested at 100 μM. No, no activity under the experimental conditions; $^a$, mol/mol; *, dimness was observed. NDGA, nordihydroguaiaretic acid; SNP, sodium nitroprusside.

3.1. Antioxidant activity of QNs using radical DPPH. Antioxidant activity was studied by the use of the stable 2,2-diphenyl-1-picrylhydrazyl radical (DPPH).[31] A freshly prepared DPPH solution (0.1 mM) exhibits a deep purple colour with an absorption maximum at 517 nm. This purple colour generally disappears in the presence of an antioxidant due to the reduction of the DPPH radical by single electron transfer (SET) from the antioxidant converted it to colourless/bleached product. Phenolic compounds, e.g. nordihydroguaiaretic acid (NDGA), giving phenoxide anions, are effective antioxidants. In this assay, we measured the initial absorbance of DPPH and the absorbance once the potential antioxidant was added. The antioxidant activity was expressed as the percentage of reducing activity. Values for QN23 and the other nitrones assayed at 100 μM were very low or without effect (Table 3) in comparison to the reference drug NDGA.

3.2. Competition of QNs with DMSO for hydroxyl radicals. Among the ROS, the hydroxyl (·OH) free radical is possibly the most toxic, as it easily reacts with biological important molecules such as DNA, lipids or carbohydrates. Polyunsaturated fatty acids are found in high concentrations in the CNS, and are particularly vulnerable to free radicals attack. Thus, we tried to test the ability of our compound to scavenge hydroxyl radicals. The competition of nitrones with DMSO for ·OH, generated by the Fe3+/ascorbic acid system, expressed as percent inhibition of formaldehyde production, was used for the evaluation of their hydroxyl radical scavenging activity.32 In this experiment, nitrones 2, 18, 19, 22 and 23 showed remarkable activity at 100 μM, with values higher than the well-known antioxidant Trolox (Table 3). Note that lipophilicity is not correlated with this result, since QN23 presents very high lipophilicity values (C log P, 3.49, Table 3), whereas QNs 18, 19 and 22 had lower lipophilicity values, and nitrone 2 a very low value. Antioxidants with lipophilic character are needed to act as radical scavengers or as chain-breaking antioxidants in biological membranes.

3.3. Anti-lipid peroxidation activity of QNs. The water-soluble azo compound 2,2'-azobis(2-amidinopropane) dihydrochloride (AAPH) has been extensively used as a clean and controllable source of thermally produced alkyl peroxyl free radicals through spontaneous thermal decomposition. The use of the free radical reactions initiator AAPH is recommended as more appropriate for measuring radical-scavenging activity in vitro, because the activity of the peroxyl radicals produced by the action of AAPH shows a greater similarity to cellular activities such as lipid peroxidation. In the AAPH assay to determine the inhibition of the lipid peroxidation (ILPO), the highly reactive alkylperoxyl radicals are intercepted mainly by a hydrogen atom transfer from the antioxidant. As shown, QN23 presented limited value, where QNs 19, 22 and 24 presented very high values (Table 3).

3.4. ABTS·+ antioxidant activity of QNs. The ABTS·+ radical cation, derived from the oxidation of 2,2'-azino-bis (3-ethylbenzothiazoline-6-sulphonic acid) (ABTS) by potassium persulfate, is a green-blue stable chromophore, which can be analyzed in the course of a decolorization assay. The addition of electron-donor antioxidants leads to ABTS·+ reduction. The chemistry taking place involves the direct generation of the ABTS·+ with no involvement of an intermediary radical. The cation radical is formed prior to the addition of the antioxidant and does not take place continually in the presence of the antioxidant. Again, and as shown, QN23 presented limited activity beside with 19, although the others nitrones had no activity (Table 3).

3.5. Lipoxygenase inhibition of QNs. Epidemiological studies revealed the link between reactive oxygen species, inflammation, and stroke risk. A key strategy to prevent potential damage to cellular compounds such as DNA, proteins and lipids is to reduce the free radical load. Moreover, it has been found that lipoxygenase (LOX) metabolism, as well as arachidonic acid metabolites, play an important role in ischemic injury and stroke suggesting it may contribute to both neuronal cell death and vascular injury. LOX index, a novel predictive biochemical marker for coronary heart disease and stroke. Studies have demonstrated that levels of several eicosanoids are increased in the brain following ischemia. Thus, LOX inhibitors may provide multifactorial protection against ischemic injury. The evaluation of the novel nitrone against soybean lipoxygenase LOX was accomplished by the UV-based enzyme assay described by Pontiki et al. Study of LOX inhibition values demonstrates that nitrone 23 provided only limited LOX inhibition, whereas the other nitrones tested, had similar (nitrone 22) or higher LOX inhibition values (Table 3). Most of the LOX inhibitors are often antioxidants or free radical scavengers. Herein, the anti-lipid peroxidation activity of QN23 goes in parallel to its anti-LOX activity, but this did not occur with nitrones 2 and 18 (with anti-LOX activity and without anti-lipid peroxidation activity), or nitrones 22 and 24 (with limited anti-LOX activity and high anti-lipid peroxidation activity) (Table 3).

3.6. NO Donating Activity QNs. Nitric Oxide radical is involved in a variety of pathophysiological processes, such as maintenance of the vascular tone, neuronal signaling and host response to infection. Additionally, NO may reduce inflammation connected to oxidative stress by scavenging ROS, which can adversely increase mucosal permeability and kill cells. Furthermore, it is found that NO as well as NO-derived ROS, interact with peroxidases[40] and lipoxygenases,[41] altering the generation of prostaglandins and leukotrienes, which are signaling molecules involved in inflammation.

QNs were tested in vitro for their ability to release NO by the action of a thiol co-factor. NO release with simultaneous production of cyanide occurs by action of reducing agents like thiols. L-cysteine was used as a co-factor in this in vitro biological test. The rate of NO release is affected by pH and the mechanism does not involve the intermediacy of S-nitrosothiols. Sodium nitroprusside (SNP), a source of NO, as demonstrated by the ability to nitrosate amines and ketones, was used as the reference drug. The screened compounds (final concentration 100 μM) was tested for its ability to release NO when dissolved in a phosphate buffer containing L-cysteine (pH 7.4). Air was oxidizing the initially formed NO, transforming it to nitrites, which were detected by the Griess reaction. Virtually, no formation of $NO_2^-$ was detectable in the absence of L-cysteine for the nitrones tested. The present study demonstrates that under the reported experimental conditions the NO release from QN23 and from the other nitrones is very limited (Table 3).

TABLE 4

In vivo anti-inflammatory activity of QN 23. Inhibition of Carrageenan-induced rat paw edema (ICPE %).

| Compounds | ICPE %[a] | Clog P |
|---|---|---|
| 23 | 48.5 ± 0.8* | 3.49 |
| Indomethacin | 47 ± 1.0** | 4.18 |

[a] Each value represents the mean ± SD obtained from 6 animals in two independent experiments (n = 6 × 2). In all cases, statistical significances against controls were performed by the Student's t-test
(*$p < 0.1$,
**$p < 0.01$); dose of the administered 0.01 mmol/kg.

3.7. Superoxide radical scavenging activity. Superoxide anion radical (O2•−) is less toxic than hydroxyl radical, but still one of the most known harmful toxic ROS. In physiological conditions, superoxide dismutase catalyzes its conversion to H2O2, which is the precursor for the formation of hydroxyl radicals in the presence of iron ions.43 Superoxide anion radicals O2•− and H2O2 are ROS produced in vivo through a one-electron reduction process of O2. The evaluation of superoxide anion radical scavenging activity can be determined using assays involving non-enzymatic or enzymatic production of superoxide anions. In this assay, superoxide anion radicals were generated by a hypoxanthine and xanthine oxidase reaction system, and the O2•− scavenging activity (%) has been measured spectrophotometrically. As shown in Table 3, QN23 presented very low scavenging activity (5%) at 0.1 mM compared to caffeic acid used as a standard (15%). However, QNs 18, 19, 22 and 24 showed higher O2•− scavenging activity, even higher than the caffeic acid, and note that nitrone 2 had no activity. At this point, the evaluation of the in vitro antioxidant profile of QN23 and other selected QNs, and the consequent relationship between the radical scavenging properties—in each of the particular assays—and the neuroprotection observed in OGD experiments, revealed some interesting conclusions.

In the LOX assay, the most potent nitrone was QN18 (IC50=32.5 μM; low effect on OGD) and QN19 (IC50=36.5 μM; intermediate effect on OGD), values distant from the recorded for NDGA (IC50=0.5 μM) used as reference. In the ILPO assay, strong and identical power (100%) was observed for QN22 (no effect on OGD), QN19, and QN24 (moderate effect on OGD), comparing very favorably with trolox (88%), used as reference compound. These results, together with the fact that QN23 presented limited activity in both LOX and ILPO assays, could conclude that these activities are not critical for neuroprotection against OGD. However, in the hydroxyl radical test, we detected strong capacity for QN23, 22, 19, 18 and nitrone 2 (effect from 100% to 94%) followed by QN24 (65%), the only nitrone below trolox value (73%), used as reference compound. Interestingly, QN23, the best nitrone in OGD, showed the greatest ROS-trapping power only in the hydroxyl test and was the most lipophilic molecule, with a C log P value of 3.49. In contrast, the other effective hydroxyl radical scavengers, QNs 22, 19, 18 and nitrone 2, were much less lipophilic (C log P values 0.97, 1.45, 1.96 and −2.05, respectively) and not as good as QN23 in the OGD test. Finally, QN24 with moderate effect on OGD, combined a moderate hydroxyl radical trapping power with intermediate lipophilicity (C log P, 2.73).

In the analysis of O2•−, QN22 (no effect on OGD) showed a remarkable scavenging capacity (29%) exceeding caffeic acid (15%) effect. However, its lipophilicity was quite low (C log P, 0.97), which could explain the ineffectiveness in the OGD neuroprotection test. Also, the O2•− scavenging activity, in addition to ILPO activity, could explain why QN19, with similar hydroxyl radical trapping power and ClogP value than QN18, was a neuroprotective nitrone. Finally, in the DPPH, ABTS•+ and NO2− experiments, no significant scavenging activities were detected for the selected compounds.

When comparing the selected compounds with QN23, this nitrone showed high ROS trapping power only in the hydroxyl test, although it was the unique showing scavenging activity—although with moderate values in some cases—against all radicals together with a high lipophilicity (C log P, 3.49). Remarkably, nitrone 2 (NXY-059) was only better than QN23 in the LOX assay, but its therapeutic interest was seriously compromised by the low C log P (−2.05).

In summary, we can conclude that the antioxidant profile alone is a very limited predictive approach. For instance, nitrones showing good scavenging activity in the LOX, ILPO, hydroxyl or superoxide radicals, may not show effect to neuroprotection in OGD assays, and additional features must be considered.

Figure 5:
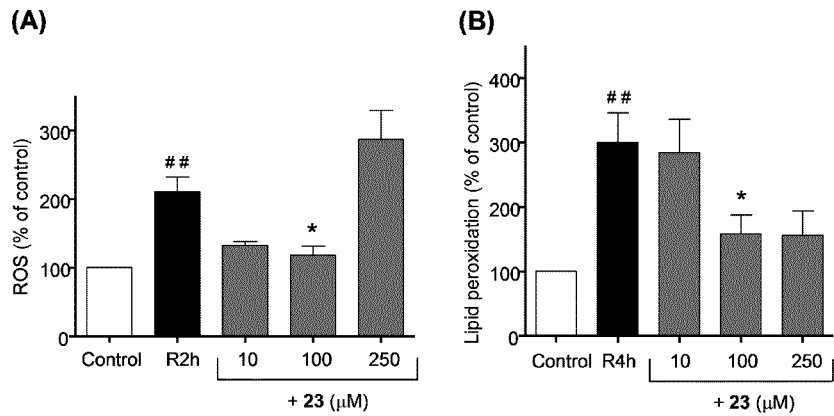
FIG. 5. Effect of QN 23 on ROS generation and lipid peroxidation induced in primary neuronal cultures subjected to OGD. (A) ROS formation was significantly diminished after treatment with QN 23. Bar graph shows the percentage of ROS generation at 2 h of recovery after OGD, either untreated (R2 h) or treated with different concentrations of QN 23, at the onset of reperfusion. The amount of ROS present in control cells was considered as 100% (white bar). (B) Nitrone 23 decreased lipid peroxidation induced in the recovery period after OGD. Bar graph shows the percentage of lipid peroxidation at 4 h of recovery after OGD, either untreated (R4 h) or treated with different concentrations of QN 23, at the onset of reperfusion. Lipid peroxidation (malondialdehyde present) in control cells was considered as 100% (white bar). In (A) and (B), results represent the mean±SE of four independent experiments. Error bars indicate SE. ##$p<0.005$, R2 h or R4 h compared with their control by one-sample t test; *$p<0.05$, compared with R2 h or R4 h by Dunnett's post test after ANOVA.

4. ROS Generation and Lipid Peroxidation Induced by Recovery After OGD Were Ameliorated by QN 23 Treatment Exposure of neuronal cultures to 4 h OGD induced significant ROS generation after 2 h recovery in normoxic and normoglycemic conditions (R2 h) (210%, $p<0.005$ compared with 100% control) (FIG. 5A). When cells were treated with QN 23 at the onset of the recovery period, ROS formation was significantly decreased to the control value (FIG. 5A). ROS generation may induce lipid peroxidation and cell membrane damage. Neuronal cultures subjected to 4 h OGD showed a significant increase of lipid peroxidation after 4 h recovery (R4 h) (300%, $p<0.005$ compared with 100% control) (FIG. 5B). When recovery was performed in the presence of QN 23, lipid peroxidation was also significantly decreased compared to R4 h value (FIG. 5B). The decrease of ROS formation and lipid peroxidation were significant at 100 µM QN 23, in accordance with the concentration at which the QN 23 had the higher neuroprotective activity against experimental ischemia in neuronal cultures (FIG. 4 and Table 1).

5. Effect of QN 23 Treatment on Neurodeficit Score Outcomes in an In Vivo Model of Cerebral Ischemia The results described above showed that QN 23 induced a significant neuroprotective effect and decreased ROS and lipid peroxidation formation in primary neuronal cultures exposed to OGD. Therefore, we decided to perform an animal model of cerebral ischemia to assay QN 23.

The experimental model used was a transient global cerebral ischemia model, in which a brief period of ischemia induces delayed neurodegeneration in the hippocampal cornu ammonis 1 (CA1) region, while cortical layers 3, 5, and 6 may be also affected. The 10-250 µM dose range of QN 23 was neuroprotective on neuronal cultures (see above), and, based on both its good solubility and good brain penetration profile, with a log BB value of 0.47 (see below), we assumed that this concentration range would be adequate in blood. The log BB, defined as the logarithm of the ratio of the concentration of a drug in the brain and in the blood, is an index of blood-brain barrier (BBB) permeability, and it was calculated with CSBBB software (ChemSilico LLC, Tewksbury, MA, USA). Accordingly, dose of 1.5 mg/kg of QN 23 was selected for the treatment of ischemic animals, which could yield 95 µM of QN 23 in blood.

Figure 6:
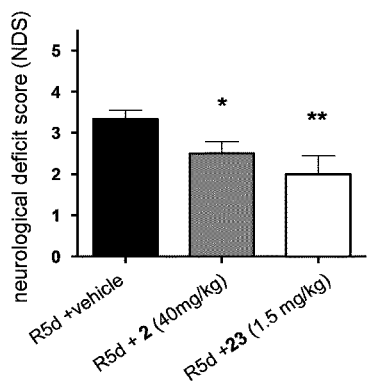
FIG. 6. Effect of QN 23 on neurodeficit score outcomes after global ischemia. Graph bars show the neurological deficit score (NDS) in ischemic animals that underwent reperfusion for 5 days, either untreated (R5 d+Vehicle) or treated with 2 (NXY-059) or 23 (R5 d+2, and R5 d+23, respectively). Data represent the mean±SE of 6-12 individual animals. Error bars indicate SE. *p<0.05, and **p<0.01, compared with R5 d+vehicle by Dunn's post test after Kruskal-Wallis' test.

Animals were subjected to 15 min of cerebral ischemia, treated with vehicle or QN 23 at the onset of reperfusion period, and studied after 5 days of reperfusion (R5 d). We evaluated the neurological deficit score (NDS) to assess the effect of QN 23 following global ischemia-reperfusion in R5 d animals. Results obtained showed that the global ischemia model affected significantly the NDS (NDS=3.3±0.21 for vehicle-treated R5 d animals, n=12) compared with sham control animals prepared in the same way without carotid occlusion (NDS=0; n=6; $p<0.0001$, by one-sample t test). QN 23 treatment, at a dose of 1.5 mg/kg, significantly decreased the NDS (2.0±0.44), decrease that was higher than the induced by 2 (NXY-059) treatment (2.5±0.28; FIG. 6). Ischemic animals were treated with nitrone 2 at a dose of 40 mg/kg, dose average of the doses assayed in experimental ischemia in rats for neuroprotection (doses ranging from 0.3 to 120 mg/kg).

6. QN 23 Treatment Induces Neuroprotection in Transient Cerebral Ischemia

Figure 7:
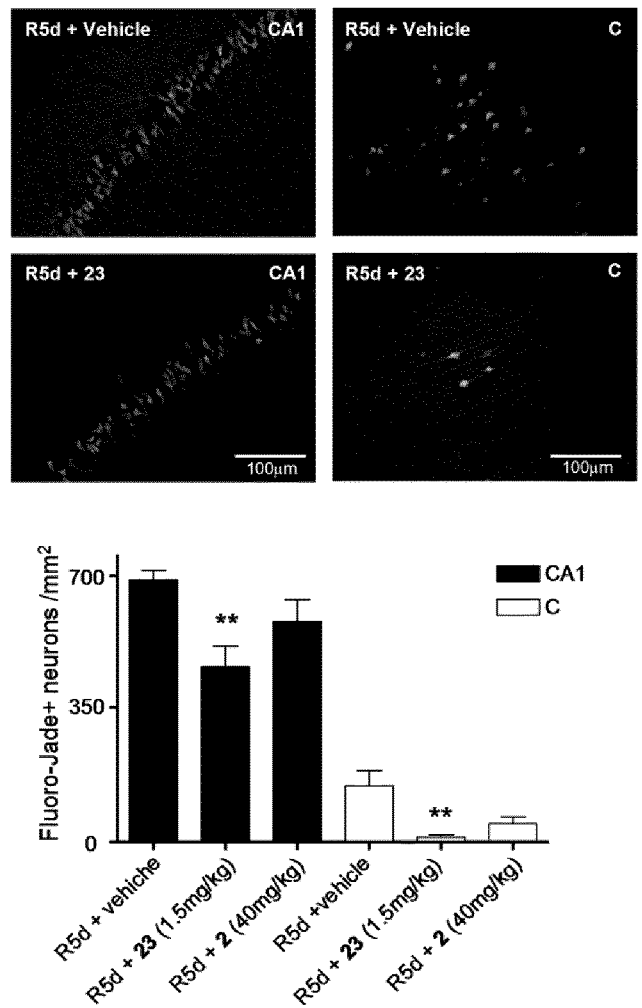
FIG. 7. QN 23 prevents the induced neuronal death after transient ischemia. Brain sections from untreated ischemic animals (vehicle), or treated with QN 23 (1.5 mg/kg) or 2 (NXY-059, 40 mg/kg) were used after fixation to detect neuronal death by Fluoro Jade B staining and visualized by fluorescence microscopy (in green). Images shown are representative results of the hippocampal CA1 (CA1) and cortical (C) regions from untreated and treated (23, 1.5 mg/kg) animals. Fluoro Jade-positive neurons were counted in CA1 or C fields as described in Methods (bar graph). Results represent the mean±SE of 6-12 individual animals. Error bars indicate SE (bar graph). **p<0.01, compared with their respective R5 d+vehicle by Dunnett's post test after ANOVA.

Animals subject to 15 min of global cerebral ischemia were treated with QN 23 by intraperitoneal injection at the onset of reperfusion period. Ischemia-induced neuronal death was evaluated after 5 days of reperfusion (R5 d) by Fluoro-Jade B staining in brain cryosections and it was observed in the hippocampal cornu ammonis 1 (CA1) region and cerebral cortex, although neuronal damage was more limited in this last region, as previously described. The results showed that the administration of QN 23 decreased neuronal death in the hippocampal CA1 region and cerebral cortex (FIG. 7). Treatment of ischemic animals with QN 23 significantly decreased neuronal death and induced neuroprotection after brain ischemia in both CA1 and cortical regions by 33% and 90%, respectively, compared with the vehicle-treated control group, whereas 2 treatment did not produce a significant effect (FIG. 7).

Figure 8:
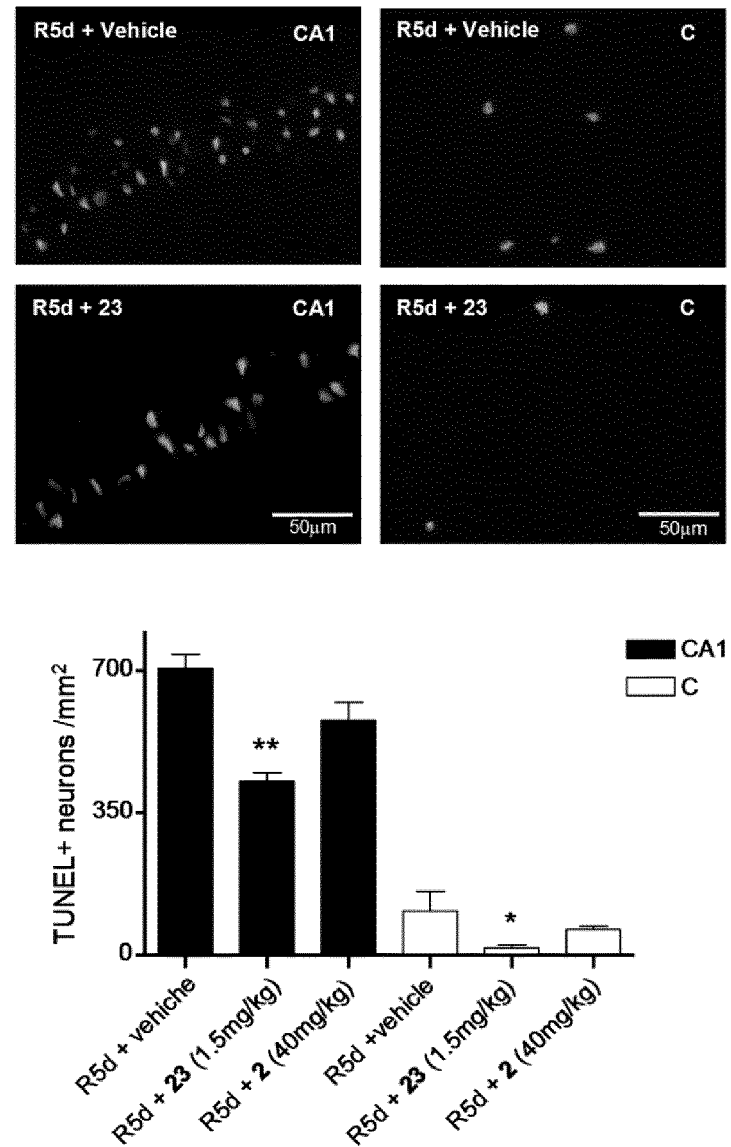
FIG. 8. Nitrone 23 decreases neuronal apoptosis after transient ischemia. Brain sections from untreated ischemic animals (vehicle), or treated with 23 (1.5 mg/kg) or 2 (NXY-059, 40 mg/kg) were used for apoptosis detection al 5 days of reperfusion following ischemia.

7. QN 23 Treatment Reduces Apoptotic Neuronal Death in Transient Cerebral Ischemia Apoptotic neuronal death can be detected by the Terminal deoxynucleotidyl transferase-mediated dUTP nick-end labeling (TUNEL) assay in the hippocampal region CA1 and cerebral cortex. Brain cryosections from R5 d animals untreated (vehicle) or treated with QN 23 were processed for apoptotic cell death detection by TUNEL assay. Results showed that administration of QN 23 after brain ischemia significantly decreased neuronal apoptosis by 39% in the CA1 region (FIG. 8). In addition, significant decrease of neuronal apoptosis by 84% was also observed in the cerebral cortex (FIG. 8). Therefore, the administration of QN 23 at 1.5 mg/kg after brain ischemia induced a significant decrease of neuronal apoptosis and neuroprotection in both hippocampal and cortical regions. Treatment with 2 (NXY-059) also induced a decrease of neuronal apoptosis, although it was not significant, in accordance with the results described above and in previous studies.

8. Effect of QN 23 Treatment on Functional Outcomes in a Transient Focal Cerebral Ischemia Model To assess the neuroprotective effect of QN 23 on experimental ischemic stroke, we induced a transient middle cerebral artery occlusion (tMCAO) and evaluated the motor deficits by grip strength test at 24 h and 48 h after the administration of QN 23. The analysis of functional outcomes confirmed an improvement in forelimb muscular strength in QN 23 treated animals. Animals treated with QN 23 at doses of 1.5 mg/kg and 2.0 mg/kg showed a significant decrease of motor deficit 48 h after treatment, compared with vehicle-treated animals (FIG. 9). Remarkably, those animals treated with the 2.0 mg/kg dose of QN 23 showed improvement in the grip strength which was significant also 24 h after treatment, compared with the vehicle group (FIG. 9). Similar studies for 2 (NXY-059) have been recently described by our group in this experimental model. In that report, ischemic animals were treated with 40 mg/kg of 2, nitrone that significantly improved the grip strength only at 48 h after treatment and in a lesser fashion than QN 23 (11.8% of improvement for 2, compared to 20.7% for QN 23 at 48 h after treatment).

9. QN 23 Treatment Reduces Infarct Size in Transient Focal Cerebral Ischemia Model To examine the efficacy of QN 23 treatment in animals subjected to tMCAO, the infarct size was calculated 48 h after tMCAO model induction. Our model induces a lesion restricted to a portion of the cortical region in the middle cerebral artery territory (FIG. 10A). Moreover, we tested two doses of QN 23 to perform a dose-response study. Our results showed that the size of the ischemic lesion was decreased in QN 23 treated animals, being significantly lower than in vehicle treated animals at 2.0 mg/kg QN 23 dose (FIG. 10). We compared these results with our data recently reported for the nitrone 2 (NXY-059) in this experimental model. Those results showed that treatment with 2 (40 mg/kg) did not reduce the size of the ischemic lesion. In summary, QN 23 treatment reduces the size of infarction and ameliorates functional motor deficit in mice subjected to tMCAO. These results suggest that QN 23 could be a potential neuroprotective compound against cerebral ischemia damage and may be a promising agent for the treatment of ischemic stroke.

TABLE 5

Neuroprotective activity for compounds investigated in neuronal cultures exposed to oxygen-glucose deprivation (OGD) [a]

| Compound | Concentration (µM) | Neuroprotection (%) |
| --- | --- | --- |
| 2 | 100 | 42.79 ± 2.31 |
|  | 250 | 52.90 ± 2.52 |
|  | 500 | 46.45 ± 1.10 |
| 6 | 0.5 | 8.30 ± 0.62 |
|  | 1 | 11.28 ± 1.32 |
|  | 10 | <0 |
|  | 100 | <0 |
| 7 | 1 | <0 |
|  | 10 | <0 |
|  | 100 | <0 |
|  | 250 | <0 |
| 8 | 1 | 5.46 ± 0.06 |
|  | 10 | <0 |
|  | 100 | <0 |
|  | 250 | <0 |
| 9 | 1 | 37.46 ± 1.01 |
|  | 10 | 14.44 ± 0.26 |
|  | 100 | <0 |
|  | 250 | <0 |
| 10 | 1 | <0 |
|  | 10 | <0 |
|  | 100 | <0 |
|  | 250 | <0 |
| 11 | 1 | 21.09 ± 0.31 |
|  | 10 | 36.55 ± 1.00 |
|  | 100 | <0 |
|  | 250 | 1.00 ± 0.07 |
| 12 | 1 | 37.00 ± 0.05 |
|  | 10 | 37.69 ± 0.66 |
|  | 100 | 34.43 ± 0.67 |
|  | 250 | 34.11 ± 0.15 |
| 13 | 10 | 35.90 ± 1.46 |
|  | 100 | 41.95 ± 1.86 |
|  | 250 | 29.76 ± 1.25 |
| 14 | 1 | 17.56 ± 1.11 |
|  | 10 | 23.66 ± 1.77 |
|  | 100 | <0 |
| 15 | 1 | 8.50 ± 0.18 |
|  | 5 | 1.57 ± 0.03 |
|  | 10 | <0 |
| 16 | 1 | 12.93 ± 0.34 |
|  | 10 | 34.34 ± 0.59 |
|  | 100 | <0 |
|  | 250 | <0 |
| 17 | 10 | 20.22 ± 1.10 |
|  | 100 | 17.65 ± 1.35 |
|  | 250 | 10.87 ± 0.88 |
| 18 | 1 | 9.76 ± 0.84 |
|  | 10 | 29.02 ± 3.83 |
|  | 100 | <0 |
| 20 | 1 | 32.77 ± 2.72 |
|  | 10 | <0 |
|  | 100 | <0 |
| 21 | 1 | <0 |
|  | 10 | 24.23 ± 0.36 |
|  | 100 | <0 |
| 22 | 0.3 | <0 |
|  | 1 | <0 |
|  | 10 | <0 |
|  | 100 | <0 |
|  | 250 | <0 |
| 24 | 0.3 | <0 |
|  | 1 | 31.30 ± 1.38 |
|  | 10 | 29.71 ± 1.38 |
|  | 100 | 38.86 ± 1.31 |
| 25 | 1 | 25.15 ± 0.14 |
|  | 10 | <0 |
|  | 100 | <0 |
|  | 250 | <0 |
| 26 | 1 | 41.72 ± 0.30 |
|  | 10 | 37.66 ± 0.52 |
|  | 100 | <0 |
|  | 250 | 0.35 ± 0.02 |
| 27 | 1 | 26.62 ± 0.37 |
|  | 10 | 28.02 ± 1.15 |
|  | 100 | 19.43 ± 1.51 |
| 28 | 1 | 35.08 ± 0.84 |
|  | 10 | 38.65 ± 0.55 |
|  | 100 | 44.27 ± 0.39 |
| 29 | 0.3 | 8.28 ± 0.51 |
|  | 1 | <0 |
|  | 10 | <0 |
|  | 100 | <0 |
| 30 | 0.3 | 13.03 ± 0.47 |
|  | 1 | 37.47 ± 1.94 |
|  | 10 | <0 |
|  | 100 | <0 |
| 31 | 1 | 7.64 ± 0.14 |
|  | 10 | 9.84 ± 0.65 |
|  | 100 | 5.83 ± 0.56 |
| 32 | 1 | <0 |
|  | 10 | <0 |
|  | 100 | <0 |

[a] Neuroprotection was defined as the percentage to reach the control value (defined as 100%) from R24 h value (defined as 0%). Data represented as mean ± SE. No neuroprotection data were found above 2 (NXY-059, 250 µM) value.

The invention claimed is:

1. The compound (Z)—N-t-butyl-1-(2-chloro-6-methoxy-quinolin-3-yl)methanimine oxide of formula (II) or a salt or hydrate thereof:

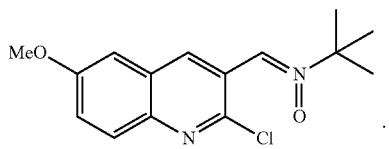

Formula II

2. A pharmaceutical composition comprising the compound as defined in claim 1, at least one pharmaceutically suitable excipient, and optionally a thrombolytic agent.

3. The pharmaceutical composition according to claim 2, wherein the thrombolytic agent is a tissue plasminogen activator (tPA) or a recombinant tissue plasminogen activator (rtPA).

4. A method for treating cerebral stroke or ischaemia in a subject, the method comprising administering to the subject the compound of claim 1.

5. The method of claim 4, wherein the method is an adjuvant therapy administered simultaneously, alternatively or successively with respect to a first-line therapy for the treatment of cerebral ischaemia or stroke.

6. The method of claim 4, wherein the method is an adjuvant therapy administered simultaneously, alternatively or successively with respect to a thrombolytic agent for the treatment of cerebral ischaemia or stroke, a thrombectomy procedure suitable for the treatment of cerebral ischaemia or stroke, or a combination thereof.

7. The method of claim 6, wherein the method is an adjuvant therapy administered simultaneously, alternatively or successively with respect to a thrombolytic agent for the treatment of cerebral ischaemia or stroke, and the thrombolytic agent is a tissue plasminogen activator (tPA) or a recombinant tissue plasminogen activator (rtPA).

* * * * *